(12) United States Patent
Mehlen et al.

(10) Patent No.: US 9,895,439 B2
(45) Date of Patent: Feb. 20, 2018

(54) COMBINED TREATMENT WITH NETRIN-1 INTERFERING DRUG AND CHEMOTHERAPEUTIC DRUG

(71) Applicant: NETRIS PHARMA, Lyons (FR)

(72) Inventors: Patrick Mehlen, Genas (FR); Andréa Paradisi, Saint Quentin Fallavier (FR); Pascale Nony, Lyons (FR)

(73) Assignee: NETRIS PHARMA, Lyons (FR)

( * ) Notice: Subject to any disclaimer, the term of this patent is extended or adjusted under 35 U.S.C. 154(b) by 0 days.

(21) Appl. No.: 14/427,426

(22) PCT Filed: Sep. 12, 2013

(86) PCT No.: PCT/EP2013/068937
§ 371 (c)(1),
(2) Date: Mar. 11, 2015

(87) PCT Pub. No.: WO2014/041088
PCT Pub. Date: Mar. 20, 2014

(65) Prior Publication Data
US 2015/0246116 A1    Sep. 3, 2015

Related U.S. Application Data

(60) Provisional application No. 61/700,158, filed on Sep. 12, 2012.

(30) Foreign Application Priority Data

Sep. 12, 2012   (EP) ..................................... 12306100

(51) Int. Cl.
| | |
|---|---|
| *A61K 39/395* | (2006.01) |
| *A61K 31/513* | (2006.01) |
| *A61K 31/704* | (2006.01) |
| *A61K 45/06* | (2006.01) |
| *A61K 31/337* | (2006.01) |
| *A61K 31/713* | (2006.01) |
| *A61K 33/24* | (2006.01) |
| *A61K 31/282* | (2006.01) |
| *A61K 31/7105* | (2006.01) |
| *A61K 31/395* | (2006.01) |
| *A61K 38/17* | (2006.01) |

(52) U.S. Cl.
CPC ........ *A61K 39/3955* (2013.01); *A61K 31/282* (2013.01); *A61K 31/337* (2013.01); *A61K 31/395* (2013.01); *A61K 31/513* (2013.01); *A61K 31/704* (2013.01); *A61K 31/713* (2013.01); *A61K 31/7105* (2013.01); *A61K 33/24* (2013.01); *A61K 38/177* (2013.01); *A61K 39/395* (2013.01); *A61K 45/06* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,312,243 B1 * | 12/2007 | Pravda | ................... A61K 31/12 424/653 |
| 7,999,072 B2 | 8/2011 | Plouet et al. | |
| 8,168,593 B2 | 5/2012 | Plouet et al. | |
| 2006/0019896 A1 | 1/2006 | Li et al. | |
| 2006/0025335 A1 | 2/2006 | Kinane et al. | |
| 2006/0153840 A1 | 7/2006 | Eichmann et al. | |
| 2008/0038255 A1 | 2/2008 | Power et al. | |
| 2009/0226458 A1 | 9/2009 | Mehlen et al. | |
| 2010/0040622 A1 | 2/2010 | Li et al. | |
| 2010/0183588 A1 | 7/2010 | Plouet et al. | |
| 2010/0221262 A1 | 9/2010 | Koch et al. | |
| 2011/0280876 A1 | 11/2011 | Plouet et al. | |
| 2012/0015364 A1 | 1/2012 | Mehlen et al. | |
| 2013/0336972 A1 | 12/2013 | Klein et al. | |

FOREIGN PATENT DOCUMENTS

| | | |
|---|---|---|
| WO | WO 02/33080 | 4/2002 |
| WO | WO 2009/141440 | 11/2009 |
| WO | 2010059821 | * 5/2010 |
| WO | 2010/079230 | * 7/2010 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979.*
Dillman J. Clinical Oncology vol. 12 p. 1497 (1994).*
Christiansen et al, Molecular Therapeutics col. 3 p. 1493 (2004).*
Li et al Expert Opin. Biol. Ther. vol. 7 p. 319 (2007).*
Wiesenthal (http://weisenthal.org/feedback. html, Feb. 4, 2002) 2 pages.*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*
International Search Report for PCT/EP2013/068937 dated Mar. 7, 2014.
Delloye-Bourgeois Celine et al: "Interference with netrin-1 and tumor cell death in non-small cell lung cancer", National Cancer Institute Journal (Online), Oxford University Press, GB, vol. 101, No. 4, (Feb. 18, 2009), pp. 237-247.
LV Dan et al: "Genetic and epigenetic control of UNC5C expression in human renal cell carcinoma.", European Journal of Cancer (Oxford, England: 1990) Sep. 2011, vol. 47, No. 13, (Sep. 2011), pp. 2068-2076.

(Continued)

*Primary Examiner* — Sheela J. Huff
(74) *Attorney, Agent, or Firm* — B. Aaron Schulman, Esq.; Stites & Harbison, PLLC

(57) ABSTRACT

Pharmaceutical composition comprising a chemotherapeutic drug and a netrin-1 interfering drug or a vector capable of expressing a netrin-1 interfering drug in vivo, in a pharmaceutically acceptable carrier or vehicle. The chemotherapeutic drug is selected from those able to induce over expression of netrin-1 in cancer cells. The combination is associated with synergic anti-cancer effect.

4 Claims, 21 Drawing Sheets

(56) References Cited

OTHER PUBLICATIONS

Figure 1:
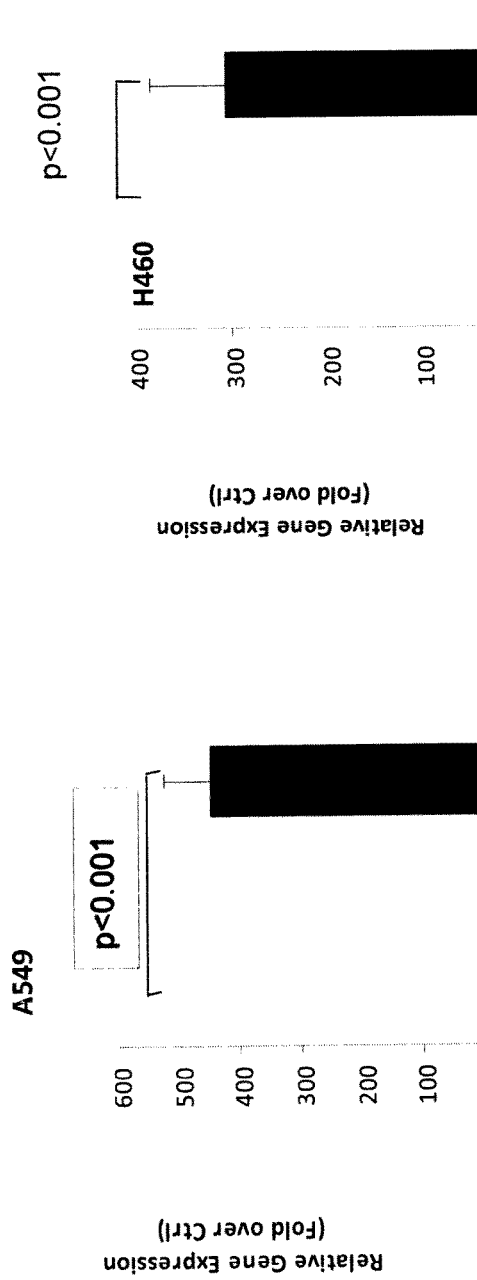

Thiebault K et al:"The netrin-1 receptors UNC5H are putative tumor suppressors controlling cell death commitment", Proceedings of the National Academy of Sciences, National Academy of Sciences, US, vol. 100, No. 7, (Apr. 1, 2003) pp. 4173-4178.

Fitamant Julien et al: "Netrin-1 expression confers a selective advantage for tumor cell survival in metastatic breast cancer", Proceedings of the National Academy of Sciences—PNAS, National Academy of Sciences, US, vol. 105, No. 12, (Mar. 25, 2008-), pp. 4850-4855.

Ackerman Susan L et al: "The mouse rostral cerebellar malformation gene encodes an UNC-5-like protein" Nature, Nature Publishing Group, vol. 386, (Apr. 24, 1997), pp. 838-842.

Bordeaux, Marie Claire et al: "The RET proto-oncogene induces apoptosis: a novel mechanism for Hirschsprung disease", The EMBO Journal, European Molecular Biology Organization, vol. 19, No. 15, (2000), pp. 4056-4063.

Bredesen, DE et al: "Receptors that mediate cellular dependence", Cell Death and Differentiation, Nature Publishing Group, (2005), pp. 1031-1043.

Aslakson Cheryl J. et al: "Selective Events in the Metastatic Process Defined by Analysis of the Sequential Dissemination of Subpopulations of a Mouse Mammary Tumor", Cancer Research, (Mar. 15, 1992), pp. 1399-1405.

De Kok Jacques B et al: "Normalization of gene expression measurements in tumor tissues: comparison of 13 endogenous control genes", Laboratory Investigation, USCAP, Inc. vol. 85, (2005), pp. 154-159.

Bernet, A. et al: "Netrine-1 and its dependence receptors: role in colorectal cancers", Pathologie Biologie, Elsevier, vol. 53, (2005), pp. 328-333.

Chan, S.S.-T. et al: "UNC-40, A C. elegans Homolog of DCC (Deleted in Colorectal Cancer), is Required in Motile Cells Responding to UNC-6 Netrin Cues", Cell, Cell Press, vol. 87, (Oct. 18, 1996), pp. 187-195.

De Cremoux, P et al: "Inter-laboratory quality control for hormone-dependent gene expression in human breast tumors using real-time reverse transcription-polymerase chain reaction", Enocrine-Related Cancer, Society for Endocrinology, GB, vol. 11, (2004), pp. 489-495.

Bernet Agnes, et al: "Inactivation of UNC5C Netrin-1 Receptor is Associated With Progression in Colorectal Malignancies", Gastroenterology, AGA Institute, vol. 133, No. 6, (2007), pp. 1840-1848.

Andre Fabrice, et al: "Breast Cancer With Synchronous Metastases: Trends in Survival During a 14-Year Period", Journal of Clinical Oncology, American Society of Clinical Oncology, vol. 22, No. 16, (Aug. 16, 2004), pp. 3302-3308.

Fazeli Amin et al: "Phenotype of mice lacking functional Deleted in colorectal cancer (Dcc) gene" Nature, Nature Publishing Group, vol. 386, (Apr. 24, 1997), pp. 796-804.

Fearon Eric R., et al: "Identification of a Chromosome 18q Gene That is Altered in Colorectal Cancers", Science (Online), vol. 247, (Jan. 5, 1990), pp. 49-56.

Ellerby Lisa M., et al: "Kennedy's Disease: Caspase Cleavage of the Androgen Receptor is a Crucial Event in Cytotoxicity", Journal of Neurochemistry, International Society for Neurochemistry, US, vol. 72, No. 1, (1999), pp. 185-195.

Hong Kyonsoo, et al: "A Ligand-gated Association between Cytoplasmic Domains of UNC5 and DCC Family Receptors Converts Netrin-Induced Growth Cone Attraction to Repulsion" Nature, Nature Publishing Group, vol. 97, (Jun. 25, 1999), pp. 927-941.

Forcet Christelle, et al: "Netrin-1-mediated axon outgrowth requires deleted in colorectal cancer-dependent MAPK activation" Nature, Nature Publishing Group, vol. 417, (May 23, 2002), pp. 443-447.

Hedgecok Edward M., et al: "The unc-5, unc-6, and unc-40 Genes Guide Circumferential Migrations of Pioneer Axons and Mesodermal Cells on the Epidermis in C. elegans", Neuron, Cell Press, vol. 2, (1990), pp. 61-85.

Geisbrechtt Brian V., et al: "Netrin Binds Discrete Subdomains of DCC and UNC5 and Mediates Interactions between DCC and Heparin", Journal of Biological Chemistry, The American Society for Biochemistry and Molecular Biology Inc. , vol. 273, No. 35, (Aug. 29, 2003), pp. 32561-32568.

Keino-Masu Kazuko, et al: "Deleted in Colorectal Cancer (DCC) Encodes a Netrin Receptor" Cell, Cell Press, vol. 87, (Aug. 16, 1996), pp. 175-185.

Boaz Inbal, et al: "DAP kinase links the control of apoptosis to metastasis" Nature, Macmillan Publishers Ltd, vol. 390, (Nov. 13, 1997), pp. 180-184.

Kinzler Kenneth W., et al: "Lessons from Hereditary Colorectal Cancer" Cell, Cell Press, vol. 87, (Oct. 18, 1996), pp. 159-170.

Kruger Robert P., et al: "Mapping Netrin Receptor Binding reveals Domains of Unc5 regulating Its Tyrosine Phosphorylation", Journal of Neuroscience, Society for Neuroscience, vol. 24, No. 48, (Dec. 1, 2004), pp. 10826-10834.

Llambi Fabien et al: "The dependence receptor UNC5H2 mediates apoptosis through DAP-kinase", The EMBO Journal, European Molecular Biology Organization, (2005), pp. 1-10.

Llambi Fabien et al: "Netrin-1 acts as a survival factor via its receptors UNC5H and DCC", The EMBO Journal, European Molecular Biology Organization, vol. 20, No. 11, (2001), pp. 2715-2722.

Lu Xiaowef, et al: "The netrin receptor UNC5B mediates guidance events controlling morphogenesis of the vascular system" Nature, Nature Publishing Group, vol. 432, (Nov. 11, 2004), pp. 179-186.

Liu Yuru, et al: "Novel Role for Netrins in Regulating Epithelial Behavior during Lung Branching Morphogenesis", Current Biology, Elsevier Ltd., vol. 14, (May 25, 2004), pp. 897-905.

Latil Alain, et al: "Quantification of Expression of Netrins, Slits and Their Receptors in Human Prostate Tumors", International Journal of Cancer, Wiley-Liss, Inc., vol. 103, (2003), pp. 306-315.

Matsunaga Eiji: "RGM and its receptor neogenin regulate neuronal survival" Nature Cell Biology, Nature Publishing Group, vol. 6, No. 8, (Aug. 2004), pp. 749-755.

Mehlen, Patrick, et al: "The DCC gene product induces apoptosis by a mechanism requiring receptor proteolysis" Nature, Macmillan Publishers Ltd, vol. 395, (Oct. 22, 1998), pp. 801-804.

Mazelin Laetitia, et al: "Netrin-1 controls colorectal tumorigensis by regulating apoptosis" Nature, Nature Publishing Group, vol. 431, (Sep. 2, 2004), pp. 80-84.

Rabizadeh Shahrooz, et al: "Induction of Apoptosis by the Low-Affinity NGF Receptor", Science, Society for Neuroscience, vol. 261, No. 48, (Jul. 16, 1993), pp. 345-348.

Muppidi Jagan R., et al: "Life and Death Decisions: Secondary Complexes and Lipid Rafts in TNF receptor Family Signal Transduction", Immunity, (Cell Press 2004), vol. 21, (Oct. 2004), pp. 461-465.

Mehlen P., et al: "The dependence receptor hypothesis", Apoptosis, (Kluwer Academic Publishers 2004), vol. 9, No. 1. (Oct. 2004), pp. 37-49.

Mehlen P., et al: "Netrin-1: when a neuronal guidance cue turns out to be a regulator of tumorigenesis", CMLS Cellular and Molecular Life Sciences, (Birkhauser Veriag, Basel 2005), pp. 1-18.

Paradisa Andrea, et al: "Netrin-1 up-regulation in inflammatory bowel diseases is required for colorectal cancer progression", PNAS Early Edition (Online) pp. 1-6, (2009).

Nguyen Andrew, et al: "Netrin-1 induces angiogenesis via a DCC-dependent ERK1/2-enos feed-forward mechanism", PNAS, (National Academy of Sciences of the USA 2006), vol. 103, No. 17 (Apr. 25, 2006) pp. 6530-6535.

Stupack Dwayne G., et al: "Potentiation of neuroblastoma metastasis by loss of caspase-8" Nature, Nature Publishing Group, vol. 439, (May 1, 2006), pp. 95-99.

Serafini Tito, et al: "Netrin-1 is Required for Commissural Axon Guidance in the Developing Vertebrate Nervous System" Cell, Cell Press, vol. 87, (Dec. 13, 1996), pp. 1001-1014.

Tanikawa Chizu, et al: "p53RDL1 regulates p53-dependent apoptosis" Nature Cell Biology (Online), Nature Publishing Group, vol. 5, (Mar. 2003), pp. 216-223.

Thibert Chantal, et al: "Inhibition of neuroepithelial Patched-Induced Apoptosis by Sonic Hedgehog", Science (Online), vol. 301, (Aug. 8, 2003), pp. 843-846.

(56) References Cited

OTHER PUBLICATIONS

Serafini Tito, et al: "The Netrins Define a Family of Axon Outgrowth-Promoting Proteins Homologous to C. elegans UNC-6" Cell, Cell Press, vol. 75, (Aug. 12, 1994), pp. 408-424.
Srinivasan Karpagam, et al: "Netrin-1/Neogenin Interaction Stabilizes Multipotent Progenitor Cap Cells during Mammary Gland Morphogenesis" Developmental Cell, Cell Press, vol. 4, (Mar. 2003), pp. 371-382.
Stein Elke, et al: "Binding of DCC by Netrin-1 to Mediate Axon Guidance Independent of Adenosine A2B Receptor Activation", Science (Online), vol. 291, (Mar. 9, 2001), pp. 1976-1982.
Stupack, Dwayne G., et al: "Apoptosis of adherent cells by recruitment of caspase-8 to unligated integrins", Journal of Cell Biology, Rockefeller University Press, vol. 155, No. 3 (Oct. 29, 2001), pp. 459-470.
Yang Xiaolu, et al: "Autoproteolytic Activation of Pro-Caspases by Oligomerization" Molecular Cell, Cell Press, vol. 1, (Jan. 1998), pp. 319-325.
Won Park Kye, et al: "The axonal attractant netril-1 is an angiogenic factor", PNAS, (National Academy of Sciences of the USA), vol. 101, No. 46 (Nov. 16, 2004) pp. 16210-16215.
Wang J.L. James, et al: "Dimerization-dependent Block of the Proapoptotic Effect of p75NTR", Journal of Neuroscience Research, Wiley-Liss, Inc., vol. 60, (2000), pp. 587-593.
Wilson Brent D., et al: "netrins Promote Developmental and Therapeutic Angiogenesis", Science (Online), vol. 313, (Apr. 8, 2006), pp. 640-644.
Yebra Mayra, et al: "Recognition of the Neural Chemoattractant Netrin-1 by Integrins $\alpha6\beta4$ and $\alpha3\beta1$ regulates Epithelial Cell Adhesion and Migration" Developmental Cell, Cell Press, vol. 5, (Nov. 2003), pp. 695-707.
Li, et al, "Rac1 and Cdc42 but Not RhoA or Rho Kinase Activities are Required for Neurite Outgrowth Induced by the Netrin-1 Receptor DCC (Deleted in Colorectal Cancer) in N1E-115 Neuroblastoma Cells", Apr. 26, 2002, pp. 15207-15214, vol. 277, No. 17, The Journal of Biological Chemistry.
Rajasundari, et al., "Netrin-1 overexpression in kidney proximal tublar epithelium ameliorates cisplatin nephrotoxicity", 2011, pp. 1717-1726, vol. 91, No. 12, Lab Invest.
Paradisi, et al., "Nf-κB Regulates Netrin-1 Expression and Affects the Conditional Tumor Suppressive Activity of the Netrin-1 Receptors", 2008, pp. 1248-1257, vol. 135, Gastroenterology.
Ozmadenci, et al, "Netrin-1 regulates somatic cell reprogramming and pluripotency maintenance", Jul. 8, 2015, pp. 1-11, 6: 7398, Nature Communications.
Wang, et al., "Netrin-1 Overexpression Protects Kidney from Ischemia Reperfusion Injury by Suppressing Apoptosis", Sep. 2009, pp. 1010-1018, vo. 175, No. 3, The American Journal of Pathology.
Zhu, et al. "Dependence receptor UNC5D mediates nerve growth factor depletion-induced neuroblastoma regression", 2013, pp. 2935-2947, vol. 123, No. 7, J Clin Invest.
Mille, et al., "Interfering with multimerization of netrin-1 receptors triggers tumor cell death", 2009, pp. 1344-1351, vol. 16, Cell Death and Differentiation.
Rama, et al., "Amyloid Precursor Protein Regulates Netrin-1-mediated Commissural Axon Outgrowth", Aug. 24, 2012, pp. 30014-30023, vol. 287, No. 35, The Journal of Biological Chemistry.
Paradisi, et al., "Netrin-1 up-regulation in inflammatory bowel diseases is required for colorectal cancer progression", Oct. 6, 2009, pp. 17146-17151, vol. 106, No. 40, PNAS.
Paradisi, et al., "Combining chemotherapeutic agents and netrin-1 interference potentiates cancer cell death", 2013, pp. 1821-1834, EMBO Mol Med.
Mehlen, et al., "Novel roles for Slits and netrins: axon guidance cues as anticancer targets?", Mar. 2011, pp. 188-197, vol. 11, Nature Reviews/Cancer.
Mehlen, et al., "Netrin-1 and its dependence receptors as original targets for cancer therapy", 2010, pp. 46-54, vol. 22, Current Opinion in Oncology.

Maisse, et al., Lipid raft localization and palmitoylation: Identification of two requirements for cell death induction by the tumor suppressors UNC5H, 2008, pp. 2544-2552, Experimental Cell Research.
Tang, et al., "Netrin-1 Mediates Neuronal Survival Through Pike-L Interaction with the Dependence Receptor UNC5B", Jun. 2008, pp. 698-706, vol. 10, No. 6, Nat Cell Biol.
Harter, et al., "Netrin-1 Expression is an Independent Prognostic Factor for Poor Patient Survival in Brain Metastases", Mar. 2014, pp. 1-10, vol. 9, No. 3, PLOS ONE.
Lourenco, et al., "Netrin-1 interacts with amyloid precursor protein and regulates amyloid-β production", 2009, pp. 655-663, vol. 16, Cell Death and Differentiation.
Luchino, et al., "Semaphorin 3E Suppresses Tumor Cell Death Triggered by the Plexin D1 Dependence Receptor in Metastatic Breast Cancer", Nov. 11, 2013, pp. 673-685, Cancer Cell 24.
Herincs, et al., "DCC association with lipid rafts is required for netrin-1-mediated axon guidance", 2005, pp. 1687-1692, vol. 118, No. 8, Journal of Cell Science.
Delloye-Bourgeois, et al., "Nucleolar Localization of a Netrin-1 Isoform Enhancers Tumor Cell Proliferation", Aug. 7, 2012, pp. 1-15, vol. 5, issue 236, Science Signaling.
Guenebeaud, et al., "The Dependence Receptor UNC5H2/B Triggers Apoptosis via PP2A-Mediated Dephosphorylation of DAP Kinase", Dec. 22, 2010, pp. 863-876, Molecular Cell 40.
Grandin, et al., "Structural Decoding of the Netrin-1/UNC5 Interactions and its therapeutical Implications in Cancers", Feb. 8, 2016, pp. 173-185, Cancer Cell 29.
Gibert, et al., "Dependence Receptors and Cancer: Addiction to Trophic Ligands", Dec. 15, 2015, pp. 5171-5175, vol. 75, No. 24, Cancer Res.
Furne, et al., "Netrin-1 is a survival factor during commissural neuron navigation", Sep. 23, 2008, pp. 14465-14470, vol. 105, No. 38, PNAS.
Furne, et al., "The dependence receptor DCC requires lipid raft localization for cell death signaling", Mar. 14, 2006, pp. 4128-4133, vol. 103, No. 11, PNAS.
Castets, et al., "Inhibition of Endothelial Cell Apoptosis by Netrin-1 during Angiogenesis", Apr. 21, 2009, pp. 614-620, Developmental Cell 16.
Broutier, et al., "Targeting netrin-1/DCC interaction in diffuse large B-cell and mantle cell lymphomas", 2016, pp. 96-104, vol. 8, No. 2, EMBO Molecular Medicine.
Coissieux, et al., "Variants in the Netrin-1 Receptor UNC5C Prevent Apoptosis and Increase Risk for Familial Colorectal Cancer", Dec. 2011, pp. 2039-2046, vol. 141, No. 6, Gastroenterology.
Castets, et al., "DCC constrains tumour progression via its dependence receptor activity", 2011, pp. 1-5, Nature.
Grandin, et al., "Structural Decoding of the Netrin-1/UNC5 Interaction and its Therapeutical Implications in Cancers", 2016, pp. 173-185, vol. 29, Cancer Cell.
Delloye-Bourgeois, et al., "Interference with Netrin-1 and Tumor Cell Death in Non-Small Cell Lung Cancer", 2009, pp. 237-247, vol. 101, JNCI Articles.
Mehlen, et al., "Role of netrin-I and netrin-I dependence receptors in colorectal cancers", 2005, vol. 93, pp. 1-6, British Journal of Cancer.
Delloye-Bourgeois, et al., "Netrin-1 acts as a survival factor for aggressive neuroblastoma", 2009, pp. 833-847, vol. 206, No. 4, J. Exp. Med.
Mehlen, et al., "Role of the Dependence Receptor DCC in Colorectal Cancer Pathogenesis", Aug. 15, 2004, pp. 3420-3428, vol. 22, No. 16, Journal of Clinical Oncology.
Mehlen, et al., "The dependence receptor hypothesis", 2004, pp. 37-49, vol. 9, No. 1, Apoptosis.
Paradisi, et al., "Combining chemotherapeutic agents and netrin-1 interference potentiates cancer cell death", 2013, pp. 1821-1834, vol. 5, EMBO Mol Med.
Stupack, et al., "Potentiation of neuroblastoma metastasis by loss of caspase-8", Jan. 5, 2006, pp. 95-99, vol. 439, Nature.
Christiansen, et al., "Biological impediments to monoclonal antibody-based cancer immunotherapy", Nov. 2004, pp. 1493-1501, vol. 3, No. 11, Molecular Cancer Therapeutics.

(56) References Cited

OTHER PUBLICATIONS

Bernet, et al., "Netrin-1 and its dependence receptors: role in colorectal cancers", 2005, pp. 328-333, vol. 53, Pathologie Biologie.

Forcet, et al. "The dependence receptor DCC (deleted in colorectal cancer) defines an alternative mechamism for caspase activation", Mar. 13, 2001, pp. 3416-3421, vol. 98, No. 6, PNAS.

\* cited by examiner

Fig. 5

| | NTN1 | | | |
|---|---|---|---|---|
| | Cisplatin | 5-Fluorouracil | Doxorubicin | Taxol |
| HBL100 | - | + | ++ | - |
| A549 | ++ | ++ | +++ | |
| H322 | - | - | - | - |
| H358 | - | - | - | - |
| HCT116 | - | ++ | - | - |
| HCT8 | - | - | + | - |
| SH-Sy5Y | ++ | + | +++ | + |
| IMR32 | - | - | - | - |
| U87MG | ++ | ++ | - | + |
| SF767 | - | - | ++ | - |
| MiaPacA | - | + | + | + |
| Panc-1 | - | - | - | - |
| PA-1 | - | - | + | - |
| TOV-112D | - | - | + | - |
| NIH-OVCAR3 | - | - | ++ | - |
| Positive cells (%) | 3/15 | 6/15 | 9/15 | 3/15 |
| | 20% | 40% | 60% | 20% |

Fig. 6

| | DCC | | | |
|---|---|---|---|---|
| | Cisplatin | 5-Fluorouracil | Doxorubicin | Taxol |
| HBL100 | - | - | ++ | - |
| A549 | +++ | - | ++ | - |
| H322 | +++ | +++ | +++ | ++ |
| H358 | +++ | +++ | +++ | +++ |
| HCT116 | + | - | ++ | - |
| HCT8 | - | - | ++ | - |
| SH-Sy5Y | - | - | - | - |
| IMR32 | + | - | + | + |
| U87MG | - | + | - | - |
| SF767 | - | - | ++ | - |
| MiaPacA | ++ | ++ | ++ | ++ |
| Panc-1 | ++ | ++ | +++ | + |
| PA-1 | - | - | ++ | + |
| TOV-112D | - | - | ++ | + |
| NIH-OVCAR3 | - | ++ | ++ | + |
| Positive cells (%) | 6/15 | 6/15 | 13/15 | 8/15 |
| | 40% | 40% | 87% | 53% |

Fig. 7

| | UNC5B | | | |
|---|---|---|---|---|
| | Cisplatin | 5-Fluorouracil | Doxorubicin | Taxol |
| HBL100 | - | - | + | - |
| A549 | ++ | + | ++ | + |
| H322 | - | - | + | - |
| H358 | - | - | - | - |
| HCT116 | - | + | + | - |
| HCT8 | - | - | + | - |
| SH-Sy5Y | - | - | - | - |
| IMR32 | - | - | + | - |
| U87MG | - | - | + | - |
| SF767 | - | - | + | - |
| MiaPacA | - | - | ++ | ++ |
| Panc-1 | - | - | ++ | ++ |
| PA-1 | - | - | + | - |
| TOV-112D | - | - | + | - |
| NIH-OVCAR3 | - | - | + | - |
| Positive cells (%) | 1/15 7% | 2/15 13% | 12/15 80% | 1/15 7% |

Fig. 8

| | UNC5D | | | |
|---|---|---|---|---|
| | Cisplatin | 5-Fluorouracil | Doxorubicin | Taxol |
| HBL100 | - (ne) | - (ne) | - (ne) | - (ne) |
| A549 | - | - | ++ | - |
| H322 | + | ++ | +++ | ++ |
| H358 | - | - | ++ | ++ |
| HCT116 | - | - | ++ | - |
| HCT8 | + | - | ++ | + |
| SH-Sy5Y | - | - | - | - |
| IMR32 | - | + | ++ | - |
| U87MG | - | - | ++ | - |
| SF767 | - | - | ++ | - |
| MiaPacA | ++ | ++ | ++ | ++ |
| Panc-1 | - | - | + | - |
| PA-1 | - (ne) | - (ne) | - (ne) | - (ne) |
| TOV-112D | - | - | ++ | + |
| NIH-OVCAR3 | - (ne) | - (ne) | - (ne) | - (ne) |

| Positive cells (%) | 3/15 | 3/15 | 10/15 | 5/15 |
|---|---|---|---|---|
| | 20% | 20% | 67% | 33% |

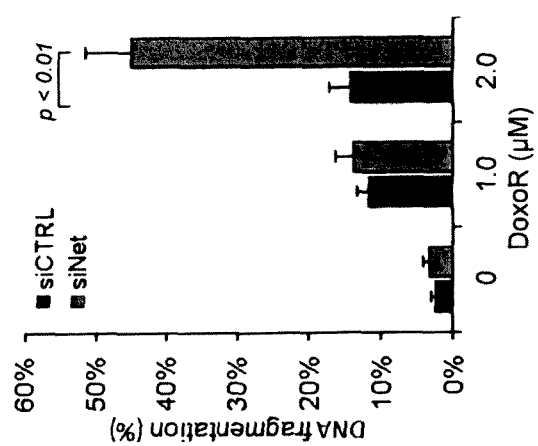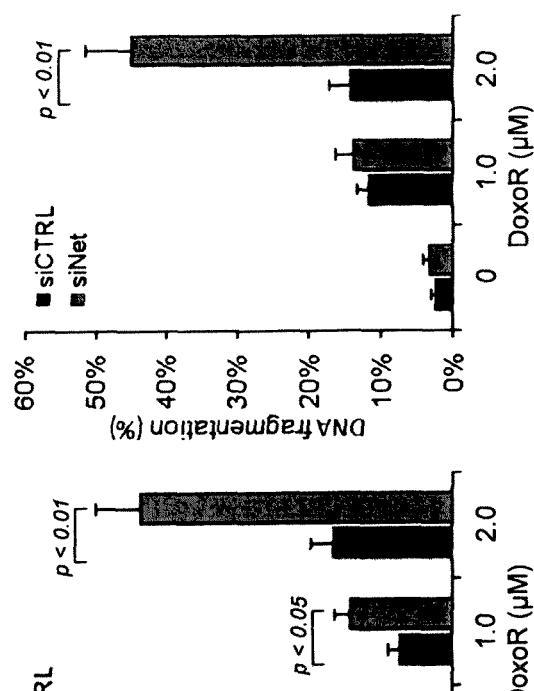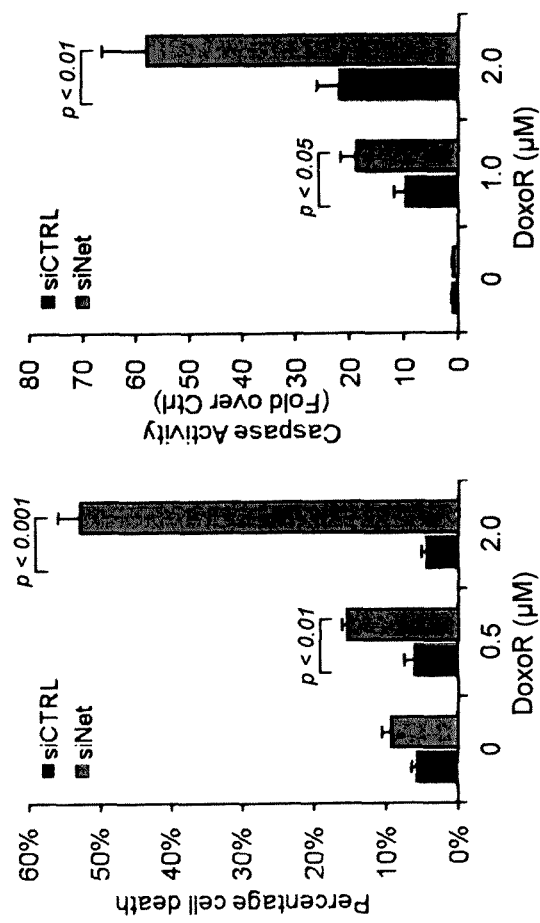

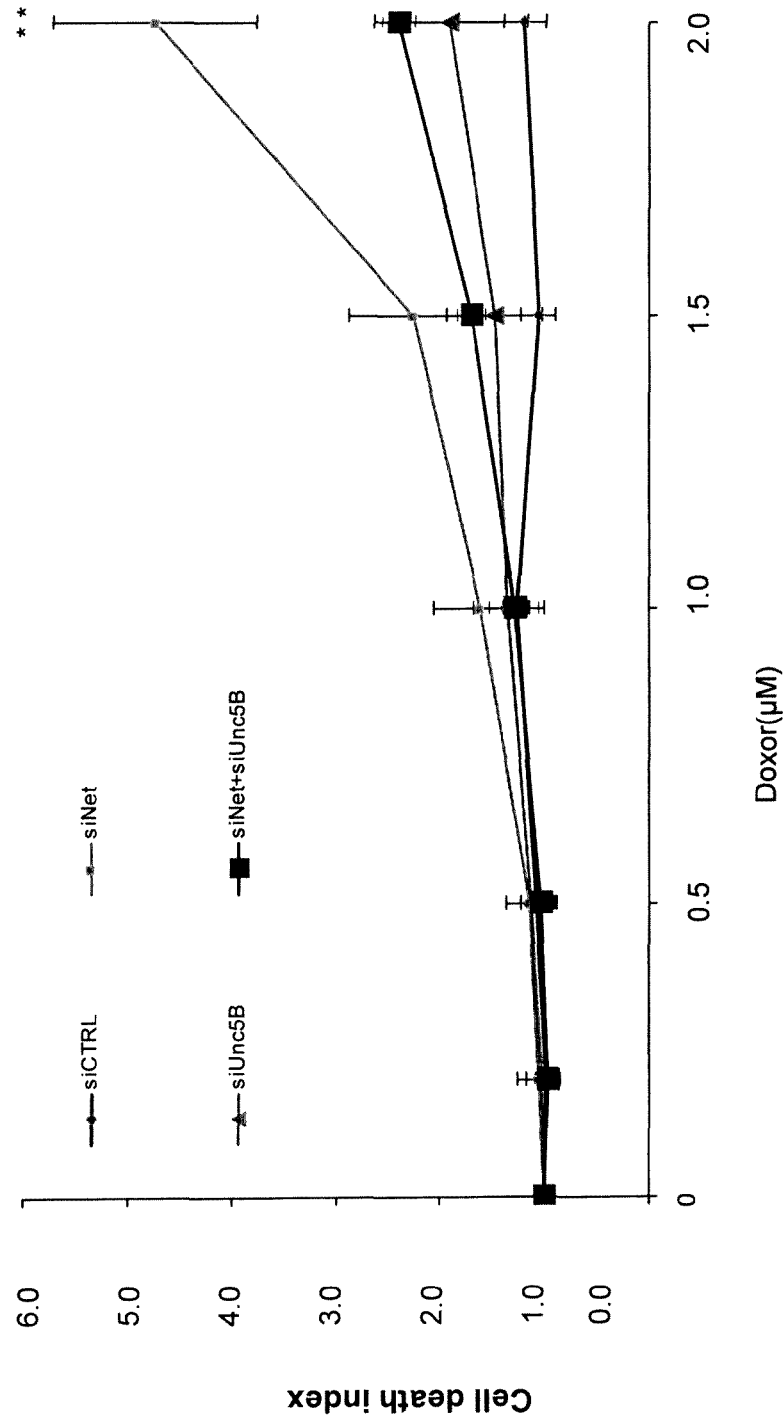

Fig. 23

| | UNC5A | | | |
|---|---|---|---|---|
| | Cisplatin | 5-Fluorouracil | Doxorubicin | Taxol |
| HBL100 | - | - | - | - |
| A549 | - | - | ++ | - |
| H322 | - (ne) | - (ne) | - (ne) | - (ne) |
| H358 | - (ne) | - (ne) | - (ne) | - (ne) |
| HCT116 | - | - | - | - |
| HCT8 | - (ne) | - (ne) | - (ne) | - (ne) |
| SH-Sy5Y | - | - | - | - |
| IMR32 | - | - | - | - |
| U87MG | - (ne) | - (ne) | - (ne) | - (ne) |
| SF767 | - (ne) | - (ne) | - (ne) | - (ne) |
| MiaPacA | ++ | ++ | ++ | ++ |
| Panc-1 | - (ne) | - (ne) | - (ne) | - (ne) |
| PA-1 | - (ne) | - (ne) | - (ne) | - |
| TOV-112D | - | - | ++ | - |
| NIH-OVCAR3 | - | - | ++ | + |

| Positive cells (%) | 1/15 | 1/15 | 4/15 | 2/15 |
|---|---|---|---|---|
| | 7% | 7% | 27% | 13% |

Fig. 24

| | UNC5C | | | |
|---|---|---|---|---|
| | Cisplatin | 5-Fluorouracil | Doxorubicin | Taxol |
| HBL100 | - | - | - | - |
| A549 | - | - | - | - |
| H322 | - | - | + | - |
| H358 | - | - | + | - |
| HCT116 | - | - | ++ | - |
| HCT8 | - (ne) | - (ne) | - (ne) | - (ne) |
| SH-Sy5Y | - | - | - | - |
| IMR32 | - | - | - | - |
| U87MG | - | - | - | - |
| SF767 | - | - | +++ | - |
| MiaPacA | - | - | - | - |
| Panc-1 | - | - | - | - |
| PA-1 | - (ne) | - (ne) | - (ne) | - (ne) |
| TOV-112D | - | - | - | - |
| NIH-OVCAR3 | - | - | - | - |
| Positive cells | 0/15 | 0/15 | 4/15 | 0/15 |
| (%) | 0% | 0% | 27% | 0% |

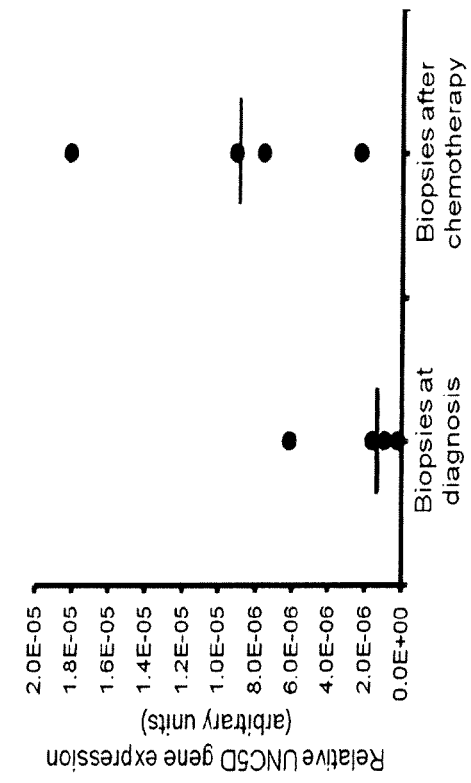
Fig. 25
Fig. 26
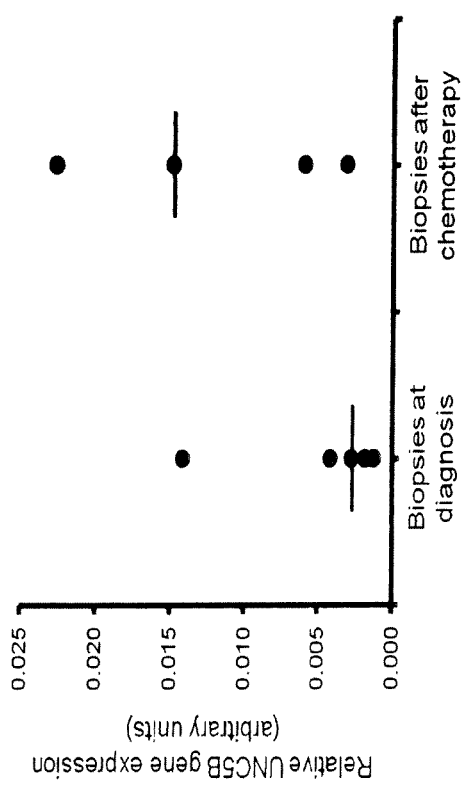
Fig. 27

Fig. 28

| | Cisplatin | | | 5-Fluorouracil | | | Doxorubicin | | | Taxol | | |
|---|---|---|---|---|---|---|---|---|---|---|---|---|
| | IC$_{10}$ | IC$_{30}$ | IC$_{50}$ | IC$_{10}$ | IC$_{30}$ | IC$_{50}$ | IC$_{10}$ | IC$_{30}$ | IC$_{50}$ | IC$_{10}$ | IC$_{30}$ | IC$_{50}$ |
| HBL100 | 0.5μM | 1.5μM | 2.5μM | 0.036μM | 0.108μM | 0.18μM | 0.04μM | 0.12μM | 0.2μM | 0.6nM | 1.8nM | 3nM |
| A549 | 10μM[1] | 25μM[2] | 50μM[3] | 0.4μM[1] | 1μM[2] | 2μM[3] | 0.5μM | 1.5μM | 2.5μM | 100nM[1] | 250nM[2] | 500nM[3] |
| H322 | 10μM[1] | 25μM[2] | 50μM[3] | 0.4μM[1] | 1μM[2] | 2μM[3] | 0.36μM | 1.08μM | 1.8μM | 1nM | 3nM | 5nM |
| H358 | 0.48μM | 1.44μM | 2.4μM | 0.4μM[1] | 1μM[2] | 2μM[3] | 0.15μM | 0.45μM | 0.75μM | 1nM | 3nM | 5nM |
| HCT116 | 7μM | 21μM | 35μM | 4μM[1] | 10μM[2] | 20μM[3] | 0.2μM | 0.6μM | 1μM | 0.08nM | 0.24nM | 0.4nM |
| HCT8 | 1.2μM | 3.6μM | 6μM | 0.25μM | 0.75μM | 1.25μM | 0.36μM | 1.08μM | 1.8μM | 4nM | 12nM | 20nM |
| SH-Sy5Y | 0.35μM | 1.05μM | 1.75μM | 0.03μM | 0.09μM | 0.15μM | 1μM[1] | 2.5μM[2] | 5μM[3] | 100nM[1] | 250nM[2] | 500nM[3] |
| IMR32 | 0.4μM | 1.2μM | 2μM | 0.4μM[1] | 1μM[2] | 2μM[3] | 0.2μM | 0.6μM | 1μM | 0.3nM | 0.9nM | 1.5nM |
| U87MG | 1.24μM | 3.72μM | 6.2μM | 0.25μM | 0.75μM | 1.25μM | 0.2μM | 0.6μM | 1μM | 2nM | 6nM | 10nM |
| SF767 | 0.4μM | 1.2μM | 2μM | 0.46μM | 1.38μM | 2.3μM | 0.24μM | 0.72μM | 1.2μM | 1nM | 3nM | 5nM |
| MiaPacA | 10μM[1] | 25μM[2] | 50μM[3] | 0.4μM[1] | 1μM[2] | 2μM[3] | 0.76μM | 2.28μM | 3.8μM | 1nM | 3nM | 5nM |
| Panc-1 | 10μM[1] | 25μM[2] | 50μM[3] | 0.4μM[1] | 1μM[2] | 2μM[3] | 1μM[1] | 2.5μM[2] | 5μM[3] | 100nM[1] | 250nM[2] | 500nM[3] |
| PA-1 | 0.12μM | 0.36μM | 0.6μM | 0.6μM | 1.8μM | 3μM | 0.16μM | 0.48μM | 0.8μM | 0.8nM | 2.4nM | 4nM |
| TOV-112D | 1.46μM | 4.4μM | 7.3μM | 4.88μM | 14.64μM | 24.4μM | 0.34μM | 1.02μM | 1.7μM | 10.4nM | 31.1nM | 51.9nM |
| NIH-OVCAR3 | 2.8μM | 8.5μM | 14.1μM | 1.72μM | 5.16μM | 8.6μM | 0.68μM | 2.04μM | 3.4μM | 6.3nM | 18.9nM | 31.5nM |

[1]: 1/5 IC$_{MAX}$; [2]: 1/2 IC$_{MAX}$; [3]: IC$_{MAX}$

COMBINED TREATMENT WITH NETRIN-1 INTERFERING DRUG AND CHEMOTHERAPEUTIC DRUG

The present invention relates to novel combined compositions and methods to treat cancer.

Netrin-1, a soluble protein initially discovered as an axon navigation cue (1), was recently proposed to play a crucial role in cancer progression by regulating apoptosis (2, 3). Indeed, netrin-1 receptors DCC and UNC5H,—i.e., UNC5H1, UNC5H2, UNC5H3 and UNC5H4 also called UNC5A, UNC5B, UNC5C or UNC5D—belong to the so-called dependence receptor family (4) (5) (6). These dependence receptors, because of their ability to induce cell death when disengaged from their ligands, create cellular states of dependence on their respective ligands (7) and, consequently, may behave as tumor suppressors because they eliminate tumor cells that would develop in settings of ligand unavailability (2, 8). Along this line, mice bearing a DCC receptor inactivated for its pro-apoptotic activity developed spontaneous colorectal cancers and were more prone to intestinal tumor progression (9). Similarly, inactivation of UNC5H3/C in mice in the gastro-intestinal tract is associated with intestinal tumor progression (10).

Thus, according to the dependence receptor paradigm, progression of aggressive human tumors should require inactivation of this death pathway. There are at least three means to achieve this survival advantage: loss of netrin-1 receptors expression, as extensively described in human colorectal cancer for DCC or/and UNC5H (10-13); loss the downstream death signaling induced by DCC or UNC5H; gain autocrine or paracrine expression of the ligand. Interestingly, netrin-1 has been shown to be up-regulated in a sizeable fraction of metastatic breast, lung, ovary and pancreatic cancer, in inflammatory associated colorectal cancer and in neuroblastoma (14-19). Proof-of concept studies, in vitro and in mice or chicken models of cancer, have shown that silencing of netrin-1 by netrin-1 siRNA or interference with netrin-1-receptors interaction are associated with tumor cell death and with inhibition of tumor growth and metastases (14-18). These later studies proposed that disrupting the netrin-1 binding to its receptors could represent an efficient anti-cancer strategy in a large fraction of cancers where netrin-1 is expressed in an autocrine or paracrine fashion. Early drug development has focused on biological agents—biologic—that mimic receptors interaction with netrin-1 (20).

Some other works focused on the role of netrin-1 and its receptors in angiogenesis with the hope that regulation of angiogenesis could help inhibiting tumor progression. US2006/0153840 discloses that modulation of netrin-1 receptor activity may activate or inhibit angiogenesis and proposes strategies to decrease or increase angiogenesis. The document discloses the use of a netrin-1 receptor or a fragment thereof as a pro-angiogenic substance, and a fusion protein comprising netrin-1 receptor and an Fc fragment of an immunoglobulin as a pro-angiogenic polypeptide as well. The document teaches that netrin-1-induced anti-angiogenic effect could be reversed by blocking availability of netrin-1 to its receptor, such as UNC5H2 (also called UNC5B), and inhibiting or blocking the netrin-1 receptor activity can induce strong angiogenesis. WO2010/059821 discloses that UNC5B is down-regulated in quiescent adult vasculature, but re-expressed during sprouting angiogenesis in implanted tumors, that stimulation of UNC5B-expressing neovessels with an agonist (Netrin-1) inhibits sprouting angiogenesis and that genetic loss of function of UNC5B may reduce Netrin-1 mediated angiogenesis inhibition. The document suggests that UNC5B activation inhibits sprouting angiogenesis and that UNC5B would be a potential anti-angiogenic target. The document then proposes the use of an anti-UNC5B antibody inhibiting an activity of UNC5B or inhibiting the binding of netrin-1 to this receptor, as an anti-angiogenic agent and as an agent to treat a disease characterized by abnormal angiogenesis, such as cancer. WO2006/054000 discloses the use of an anti-netrin-1 antibody as an anti-angiogenic agent and its use in a composition for treating cancer. Both last documents further propose to combine the anti-UNC5B or anti-netrin-1 antibody to an existing chemotherapeutic drug. In the absence of consistent experimental results in these contradictory disclosures, it is difficult for the person skilled in the art to reach some clear teaching on the incidence of anti-netrin-1 or anti-UNC5H2 antibodies on angiogenesis let alone on a potential anti-tumour activity. It is also difficult for the person skilled in the art to make a biological link between a chemotherapeutic drug that is known to affect proliferating tumor cells but not quiescent endothelial cells that form the vessels and an anti-angiogenic treatment based on an anti-netrin-1 or anti-UNC5H2 antibodies.

The present invention provides however a biological rationale for combining a treatment based on netrin-1 interference and a chemotherapeutic drug that increases, as a result of a stress response by the tumor cell, the dependency for tumor cell survival on netrin-1.

Indeed, the search of the fraction of cancer patients who would be eligible to a netrin-1 interference-based treatment during early clinical evaluation led the present inventors to examine the effect of conventional chemotherapeutic treatments on netrin-1 and netrin-1 receptors expression. Doxorubicin, 5-Fluorouracil (5FU), paclitaxel (Taxol) and Cisplatin are indeed "classic" chemotherapies and are still widely used in the management of patients with breast, lung, colorectal, as well as other types of solid tumors both in patients with localized and advanced tumors. However, despite their efficacy, the use of conventional agents is limited by toxicity and the emergence of resistance. The present inventors show here that these chemotherapeutic treatments, even though they act on different cellular mechanisms, triggers significant increase of netrin-1 and its receptors. The present inventors show that this increase is associated with an increased cell death induction upon netrin-1 interference in vitro. As a consequence the present inventors show that combination of Doxorubicin with a netrin-1 interfering drug candidate potentiates tumor growth inhibiting effect in an animal model.

The pre-clinical data showed here support the view that combining conventional drugs plus netrin-1 interference may lead to an unexpected increased efficacy with reduced concentration of conventional drugs. Together these data support the rationale that netrin-1 interference based therapy in combination with conventional chemotherapies is associated with synergic anti-cancer effect. It is deemed the netrin-1 interference based therapy has two positive effects, the first is the induction of apoptosis or cell death owing the inhibition of the netrin-1/receptor binding (the so-called promotion of netrin-1 receptors-induced apoptosis), the second is that the potentially deleterious effect of a-chemotherapy-induced increase in netrin-1 and/or receptor expression would be counter-balanced by the inhibition of netrin-1/receptor binding and its anti-apoptotic effect.

In the present invention, the compositions and methods are for the treatment of cancers expressing or over-expressing netrin-1, wherein this expression or over-expression is linked to the cancer itself, or is induced by the chemotherapeutic drug treatment alone, or both.

An object of the invention is a method of combined anti-cancer treatment comprising the administration to a patient in need thereof of a chemotherapeutic drug and of a netrin-1 interfering drug or a vector capable of expressing a netrin-1 interfering drug in vivo. The chemotherapeutic drug and the netrin-1 interfering drug are in effective amount.

Another object of the invention is a composition comprising a netrin-1 interfering drug or a vector capable of expressing a netrin-1 interfering drug in vivo for use as an anti-cancer medicament to be used in combination with a chemotherapeutic drug in a patient. The invention also relates to a composition comprising a netrin-1 interfering drug or a vector capable of expressing a netrin-1 interfering drug in vivo for use as an anti-cancer medicament in a patient who is treated with a chemotherapeutic drug.

Another object of the invention is a composition comprising a chemotherapeutic drug for use as an anti-cancer medicament to be used in a patient in combination with a netrin-1 interfering drug or a vector capable of expressing a netrin-1 interfering drug in vivo. The invention also relates to a composition comprising a chemotherapeutic drug for use as an anti-cancer medicament in a patient who is treated with a netrin-1 interfering drug or a vector capable of expressing a netrin-1 interfering drug in vivo.

Another object of the invention is a composition or kit of parts comprising a chemotherapeutic drug and a netrin-1 interfering drug or a vector capable of expressing a netrin-1 interfering drug in vivo, for a simultaneous, separate or sequential administration to a patient.

Another object of the invention is a composition or kit of parts comprising a chemotherapeutic drug and a netrin-1 interfering drug or a vector capable of expressing a netrin-1 interfering drug in vivo, for a simultaneous, separate or sequential administration to a patient, for use as an anti-cancer medicament or anti-cancer treatment.

Another object of the invention is a composition comprising a chemotherapeutic drug and a netrin-1 interfering drug or a vector capable of expressing a netrin-1 interfering drug in vivo, in a pharmaceutically acceptable carrier or vehicle.

Another object of the invention is a composition comprising a chemotherapeutic drug and a netrin-1 interfering drug or a vector capable of expressing a netrin-1 interfering drug in vivo, in a pharmaceutically acceptable carrier or vehicle, for use as an anti-cancer medicament.

Still another object is the use of a netrin-1 interfering drug or a vector capable of expressing a netrin-1 interfering drug in vivo for the preparation of an anti-cancer medicament intended for a combined treatment of a patient with a chemotherapeutic drug.

Still another object is the use of a chemotherapeutic drug for the preparation of an anti-cancer medicament intended for a combined treatment of a patient with a netrin-1 interfering drug or a vector capable of expressing a netrin-1 interfering drug in vivo.

Still another object is the use of a netrin-1 interfering drug or a vector capable of expressing a netrin-1 interfering drug in vivo and a chemotherapeutic drug for the preparation of a combined anti-cancer medicament.

Still another object is the use of a netrin-1 interfering drug or a vector capable of expressing a netrin-1 interfering drug in vivo and a chemotherapeutic drug for the preparation of a combined anti-cancer medicament composition or kit of parts, for a simultaneous, separate or sequential administration to a patient.

In accordance with an important feature of the invention and as further explained below, the chemotherapeutic drug is a drug which induces an over-expression of netrin-1 in cancer cells and the netrin-1 interfering drug promotes netrin-1 receptors-induced apoptosis or cell death.

A patient may be a mammal, and more particularly a human.

Therapeutic treatment encompasses prophylaxy and therapy.

More detailed embodiments for these objects will now be described.

The chemotherapeutic drug is in particular a drug which induces an over-expression of netrin-1 in cancer cells. The determination that a drug induces a netrin-1 over-expression may be easily performed on any cancerous cell, such as cell line or cells from a biopsy. In an embodiment, the assay is performed on cells from the cancer to be treated, for example from a biopsy. In another embodiment, the assay is performed on a cell, such as a cell line, which is representative for the cancer to be treated. In another embodiment, the assay is made on a A549 or H460 cell line. The assay may comprise comparing the netrin-1 gene expression between the cells treated with the chemotherapeutic drug and the cells not treated. The expression may be measured by PCR, especially quantitative RT-PCR, for example using the primers disclosed and provided herein (SEQ ID NO: 11 and 12). The classification of a drug in the family of those inducing this over-expression may simply be performed in accordance with the method described in the following Material and Method on a A549 or H460 cell line, by reference to FIG. 1.

The chemotherapeutic drug is especially a cytotoxic drug.

In some preferred embodiments, the drug is doxorubicin, 5-fluorouracil (5FU), paclitaxel (e.g. Taxol), or cisplatin.

In an embodiment, the drug is a cytotoxic antibiotic. The cytotoxic antibiotic may be actinomycin, an anthracycline, bleomycin, plicamycin or mitomycin. The anthracycline may be doxorubicin, daunorubicin, valrubicin, idarubicine or epirubicine.

In an embodiment, the drug is an alkylating agent. The alkylating agent may be a platinum derivative, such as cisplatin, carboplatin, oxaliplatine or other alkylating agents such as cyclophosphamide, ifosfamide, melphalan, thiotepa. Other classes include-epipodophylotoxines, e.g. etoposide, topoisomerase inhibitors (camptotecines), e.g. irinotecan, topotecan, alkylating agents of the minor groove of DNA, e.g. Trabectedine (YONDELIS), methotrexate, pemetrexed, raltitrexed.

In an embodiment, the drug is a taxane or other tubulin targeting agents. The taxane may be paclitaxel or docetaxel, or eribuline (recently approved for breast cancer).

In an embodiment, the drug is an antineoplastic agent such as:
  breast hormonotherapy agents: e.g. tamoxifene, letrozole, anastrozole, exemestane, fasldex;
  prostate hormonotherapy agents: e.g. LHRH agonists, bicalutamide, abiraterone;
  monoclonal antibodies: e.g. cetuximab, panitumumab, bevacizumab;
  kinase inhibitors: e.g. imatinib, nilotinib, dasatinib, erlotinib, gefitinib, afatinib, sunitinib, sorafenib, pazopanib, crizotinib, axitinib.

The invention does or may not imply a change of the dose regimen of the chemotherapeutic drug. However, the synergy that occurs with the netrin-1 interfering drug may allow to using lower dose regimen in a patient. The skill practitioner is able to determine the optimum dose regimen in the context of the combined treatment provided by the present invention.

The invention also concerns a combined treatment of a patient wherein the chemotherapy is already a combined chemotherapy, in the sense that at least two chemotherapeutic drugs are incorporated in the treatment protocol. That is to say that the methods, compositions, kit of parts and uses according to the different objects of the invention, combine at least one netrin-1 interfering drug and at least two (e.g. 2, 3, 4 or 5) chemotherapeutic drugs.

The netrin-1 interfering drug is a drug which interferes with the netrin-1 ability to interact with a netrin-1 receptor, or which interferes with the ability of netrin-1 to induce dimerisation or multimerization of netrin-1 receptor, or more generally which promotes netrin-1 receptors-induced apoptosis. The person skilled in the art may refer to WO2007/099133 which discloses interference between netrin-1 and its receptors, either a decrease or an inhibition of interaction or binding between netrin-1 and receptors, or a decrease or an inhibition of the ability of netrin-1 to induce dimerisation or multimerization of netrin-1 receptor, whereby netrin-1 receptors-induced apoptosis is promoted.

In an embodiment, it is a small interfering RNA or siRNA which is a double stranded RNA (dsRNA) (that may have namely from 10 to 50 nucleotides in length) and which reduces expression of the gene coding for netrin-1. Portions of the first strand are complementary to the target gene, i.e. it has sufficient complementarity to hybridize to the target gene, for example there is at least 80% identity to the target gene or to a portion thereof. AP: human Netrin-1 mRNA sequence accession number: NM_004822. siRNA sequence that may be used: SEQ ID NO: 10 AAGCUGGACGCAG-CAUGAUGC (sense), corresponding to position 94-114 of sequence NM_004822.

In a second embodiment, the interfering drug is one which binds to netrin-1 and netrin-1 is rendered unable to bind to its receptors due to the binding of the interfering drug or to induce dimerization/multimerization of the netrin-1 receptors, especially DCC and/or UNC5. In an embodiment, this drug is an antibody binding to netrin-1. It is preferably a polyclonal or monoclonal antibody specifically binding to netrin-1. In another embodiment, this drug is a compound comprising an extracellular domain of a netrin-1 receptor or a fragment of said extracellular domain. For example, the amino acid sequence of the extracellular domain of a netrin-1 receptor or a fragment of said extracellular domain are given in UniProt Sequence ID [extracellular domain position range]: UNC5A: Q6ZN44 [aas 26-306, or fragment 34-240]; UNC5B: Q8IZJ1 [aas 27-377 or fragment 29-244]; UNC5C: O95185 [aas 41-380 or fragment 61-258]; UNC5D: Q6UXZ4 [aas 33-379]; DCC: P43146 [aas 26-1097]. This drug is able to bind to netrin-1. The netrin-1 receptors may be DCC, UNC5A, UNC5B, UNC5C or UNC5D. The method of the invention may make use of two or more compounds each comprising an extracellular domain or part thereof, from a different netrin-1 receptor. For example, the drug comprises two compounds comprising an extracellular domain or part thereof, from DCC and from an UNC5, e.g. UNC5A.

In a third embodiment, the interfering drug is one which binds to a netrin-1 receptor. The netrin-1 receptors may be DCC, UNC5A, UNC5B, UNC5C or UNC5D. The method of the invention may makes use of two or more interfering drugs each one binding to a different netrin-1 receptor. For example, the drug comprises two interfering drugs, one binding to DCC and the other to an UNC5, e.g. UNC5A. In an embodiment, this drug is an antibody binding to a netrin-1 receptor. It is preferably a polyclonal or monoclonal antibody specifically binding to a netrin-1 receptor. In another embodiment, this drug is a compound, especially a compound comprising a peptidic moiety, or a small molecule, which is able to bind to a netrin-1 receptor, this binding being able to prevent netrin-1 ability to block apoptosis induction by a netrin-1 receptor, in particular to induce the dimerization or the multimerization of the receptor.

"Antibody" is used in the broadest sense to designate any antibody that may bind to netrin-1 wherein this binding impedes the binding between netrine-1 and a netrin 1 receptor.

"Antibody" includes monoclonal antibodies, polyclonal antibodies, single-chain antibodies and antigen binding fragments of these antibodies which exhibit the desired biological activity. The monoclonal antibodies may be murine, chimeric or humanized. The term "antibody" refers to any full-length antibody or functional fragment of an antibody (obtained by genetic engineering or not), comprising, or consisting of, at least one antigenic combination site, allowing said antibody to bind to at least one antigenic determinant of an antigenic compound. By way of example of antibody fragments, there may be mentioned the fragments Fab, Fab', F(ab')$_2$ and the single-chain variable fragments (scFv chains). The antibodies used in the present invention are antibodies specific for the antigen. They are preferably monoclonal antibodies or monospecific polyclonal antibodies, that is to say that they specifically recognize only one epitope. The production of monoclonal antibodies or of monospecific polyclonal sera, or of antibodies obtained by screening genomic libraries, useful in the context of the invention are conventional techniques.

An anti-netrin 1 polyclonal antibody may, inter alia, be obtained by immunizing an animal such as a rabbit, a mouse and the like with the aid of the selected amino acid sequence, collecting and then depleting the antiserum obtained on, for example, an immunoadsorbent containing the receptor according to methods known per se to a person skilled in the art.

The netrin-1 amino acid sequence (without the signal peptide) is as depicted on SEQ ID NO:13 and netrin-1 may be used in whole or in part to design antibodies.

Generally, monoclonal antibodies may be obtained according to the conventional method of lymphocyte fusion and hybridoma culture described by Köhler and Milstein, (1975). Other methods for preparing monoclonal antibodies are also known (Harlow et al., ed., 1988 "Antibodies: a laboratory manual"). The monoclonal antibodies may be prepared by immunizing a mammal (for example a mouse, a rat, a rabbit or even a human being, and the like) and using the lymphocyte fusion technique leading to hybridoma (Köhler and Milstein, 1975).

Alternative techniques to this customary technique exist. It is possible, for example, to produce monoclonal antibodies by expressing a nucleic acid cloned from a hybridoma. It is also possible to produce antibodies by the phage display technique by introducing cDNAs for antibodies into vectors, which are typically filamentous phages which exhibit gene libraries V at the surface of the phage (for example fUSE5 for *E. coli*, Scott, 1990). Protocols for constructing these antibody libraries are described in Marks et al. (1991). The cDNA corresponding to full length netrin-1 with signal sequence (SEQ ID NO: 14) or to a suitable fragment thereof is used to produce monoclonal antibodies according to these methods.

In a preferred embodiment, the interfering drug comprises an extracellular domain of a netrin-1 receptor or a fragment of said extracellular domain. The netrin-1 receptors may be DCC, UNC5A, UNC5B, UNC5C or UNC5D.

In an embodiment, the extracellular domain or part thereof is bound to an antibody Fc part. In a preferred embodiment, the Fc part is the Fc or part thereof of a human IgG. The human IgG may be namely IgG1, IgG2A, IgG2B, IgG3. In a preferred embodiment, the IgG is IgG1.

In an embodiment, the fusion protein is single chain, which means that the protein is made of a DCC or a UNC5 fragment comprising or constituted of respectively the fourth or fifth fibronectin-like domain of DCC or the two Ig-like domains of UNC5 and of a peptidic or protein sequence improving the pharmaceutical parameters of the compound.

In another preferred embodiment, the fusion protein is double chain, which means that the fusion protein is made of two chains each comprising or constituted of respectively the fourth or fifth fibronectin-like domain of DCC or the two Ig-like domains of UNC5 and of an antibody Fc part, wherein both chains are linked together, preferably by one or more, e.g. two, disulfide bonds.

In an embodiment, the drug comprises the fifth fibronectin domain (Fn5 or 5Fbn) of DCC. Preferably, the drug comprises a DCC-fusion protein comprising this Fn5 fused to an antibody Fc part. In a preferred embodiment, the Fc part is the Fc or part thereof of a human IgG. The human IgG may be namely IgG1, IgG2A, IgG2B, IgG3. In a preferred embodiment, the IgG is IgG1. The DCC gene is available for example from NCBI, under ID 1630 (as updated on Jul. 14, 2012), it encodes the DCC receptor protein as Uniprot P43146, updated Jul. 11, 2012. A DCC-fusion protein useful in the invention and comprising the Fn5 is described in WO2012025618. In an embodiment, the fusion protein has the amino acid sequence SEQ ID NO: 2, 3 or 4 in WO2012025618. In an embodiment, the fusion protein is encoded by the DNA sequence SEQ ID NO: 1 in WO2012025618. Other examples of fusion proteins comprising the Fn5 are the DCC-5-fibronectin fusion protein with Glutathione-S-transferase (DCC-5Fbn-GST) described in WO2007099133, Fitamant et al. (14) and Delloye-Bourgeois (16).

In an embodiment, the drug comprises the two Ig-like domains of a UNC5. Preferably, the drug comprises an UNC5-fusion protein comprising the two Ig-like domains of a UNC5 fused to an antibody Fc part. The human IgG may be namely IgG1, IgG2A, IgG2B, IgG3. In a preferred embodiment, the IgG is IgG1. In an embodiment, UNC5 is UNC5A. In another embodiment, UNC5 is UNC5B. In another embodiment, UNC5 is UNC5C. In still another embodiment, UNC5 is UNC5D.

In an embodiment, the UNC5A protein in UNC5A-fusion comprises or consists of the amino acids 20 to 217 of SEQ ID NO: 1. This fusion protein may further comprise the IgG1 Fc comprising or consisting of amino acids 220 to 446 of SEQ ID NO: 1. This Fc is fused to the UNC5A protein, for example through a linker, such as GT. In an embodiment, the present invention relates to an UNC5A-fusion of UNC5A protein comprising or consisting of the amino acid sequence of SEQ ID NO: 1: Kappa2 signal peptide sequence: aas 1 to 19; Ig-like domains of UNC5A: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention also encompasses variant sequences having a percentage of identity which is equal or more than 90%, preferably than 96, 95, 94, 93, 92 or 91%, on the whole length of the 20-217 amino acid sequence, or of amino acids 20-446 of SEQ ID NO: 1. Amino acid substitutions may for example occur at one or several of positions 9, 72, 74, 87, 144, 164, 170, 193 and/or 210 on the whole length of the 20-217 amino acid sequence, or of SEQ ID NO: 1.

In another embodiment, the UNC5B protein in UNC5B-fusion comprises or consists of the amino acids 20 to 215 of SEQ ID NO: 2. This fusion protein may further comprise the IgG1 Fc comprising or consisting of amino acids 218 to 444 of SEQ ID NO: 2. This Fc is fused to the UNC5A protein, for example through a linker, such as GT. In an embodiment, the present invention relates to an UNC5B-fusion of UNC5B protein comprising or consisting of the amino acid sequence of SEQ ID NO: 2: Kappa2 signal peptide sequence: aas 1 to 19; Ig-like domains of UNC5B: aas 20 to 215; Linker: aas 216-217; Human IgG1 Fc: aas 218 to 444. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-215 amino acid sequence, or of amino acids 20-444 of SEQ ID NO: 2. Amino acid substitutions may for example occur at one or several of positions 29, 74, 100, 109, 113, 146, 149, 155, 172, 184, 189, 201, 213 and/or 214 on the whole length of the 20-215 amino acid sequence, or of SEQ ID NO: 2.

In still another embodiment, the UNC5C protein in UNC5C-fusion comprises or consists of the amino acids 20 to 217 of SEQ ID NO: 3. This fusion protein may further comprise the IgG1 Fc comprising or consisting of amino acids 220 to 446 of SEQ ID NO: 3. This Fc is fused to the UNC5A protein, for example through a linker, such as GT. In an embodiment, the present invention relates to an UNC5C-fusion of UNC5C protein comprising or consisting of the amino acid sequence of SEQ ID NO: 3: Kappa2 signal peptide sequence: aas 1 to 19; Ig-like domains of UNC5C: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-217 amino acid sequence, or of amino acids 20-446 of SEQ ID NO: 3. Amino acid substitutions may for example occur at one or several of positions 33, 66, 109, 129, 136, 178, 189 and/or 211 on the whole length of the 20-217 amino acid sequence, or of SEQ ID NO: 3.

In still another embodiment, the UNC5D protein in UNC5D-fusion comprises or consists of the amino acids 20 to 217 of SEQ ID NO: 4. This fusion protein may further comprise the IgG1 Fc comprising or consisting of amino acids 220 to 446 of SEQ ID NO: 4. This Fc is fused to the UNC5A protein, for example through a linker, such as GT. In an embodiment, the present invention relates to an UNC5D-fusion of UNC5D protein comprising or consisting of the amino acid sequence of SEQ ID NO: 4: Kappa2 signal peptide sequence: aas 1 to 19; Ig-like domains of UNC5D: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-217 amino acid sequence, or of amino acids 20-446 of SEQ ID NO: 4. Amino acid substitutions may for example occur at one or several of positions 38, 79, 80, 115, 131, 178, 186, 201 and/or 212 on the whole length of the 20-217 amino acid sequence, or of SEQ ID NO: 4.

The present invention provides for the following nucleic acid molecules:
- SEQ ID NO: 5 encoding an UNC5A protein; nt (nucleotides); nt 1-6 HindIII restriction site, nt 7-15 kozak sequence, nt 16-72 kappa2 signal sequence, nt 73-666 UNC5A coding sequence, nt 667-672 XpnI restriction site;
- SEQ ID NO: 6 encoding an UNC5B protein; nt (nucleotides); nt 1-6 HindIII restriction site, nt 7-15 kozak sequence, nt 16-72 kappa2 signal sequence, nt 73-660 UNC5B coding sequence, nt 661-666 XpnI restriction site;
- SEQ ID NO: 7 encoding an UNC5C protein; nt (nucleotides); nt 1-6 HindIII restriction site, nt 7-15 kozak sequence, nt 16-72 kappa2 signal sequence, nt 73-666 UNC5C coding sequence, nt 667-672 XpnI restriction site;
- SEQ ID NO: 8, encoding an UNC5D protein; nt (nucleotides); nt 1-6 HindIII restriction site, nt 7-15 kozak sequence, nt 16-72 kappa2 signal sequence, nt 73-666 UNC5C coding sequence, nt 667-672 XpnI restriction site;
- SEQ ID NO: 9 encoding a human IgG1 Fc (hinge+CH2+CH3 DNA sequence, nt 7-693), with KpnI restriction site at positions 1-6 nt and XbaI restriction site at position 694-699.

The nucleic acid molecules of the present invention may be DNA molecules or RNA molecules. They may also be nucleic acid analogues, such as oligonucleotide thiophosphates, substituted ribo-oligonucleotides, LNA (Locked nucleic acid) molecules, PNA (Peptide nucleic acid) molecules, GNA (glycol nucleic acid) molecules, TNA (threose nucleic acid) molecules, morpholino polynucleotides, or antagomir (cholesterol-conjugated) nucleic acid molecules or any modification thereof as known in the art (see, e.g. U.S. Pat. Nos. 5,525,711, 4,711,955, 5,792,608 or EP 302 175 for examples of modifications). Nucleic acid molecules in context of the present invention may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). In context of the present invention, thymine (T) and uracil (U) may be used interchangeably depending on the respective type of nucleic acid molecule. For example, as the skilled person is well aware of, a thymine (T) as part of a DNA corresponds to an uracil (U) as part of the corresponding transcribed mRNA. The nucleic acid molecule of the present invention may be single- or double-stranded, linear or circular, natural or synthetic, and, if not indicated otherwise, without any size limitation. The nucleic acid molecule may also comprise a promoter as further detailed herein below. The promoter may be homologous or heterologous. In a particular embodiment, the nucleic acid molecule provided herein is under the control of this promoter.

Generally, as used herein, a polynucleotide comprising the nucleic acid sequence of a sequence provided herein may also be a polynucleotide consisting of said nucleic acid sequence.

The nucleic acid molecule of the present invention may be cloned into a vector. The person skilled in the art may refer to WO2007/099133 which describes vectors and methods of preparing vectors and their use, which can be used in carrying out the present invention. The term "vector" as used herein particularly refers to plasmids, cosmids, viruses, bacteriophages and other vectors commonly used in genetic engineering. In a preferred embodiment, these vectors are suitable for the transformation of cells, eukaryotic cells like fungal cells, cells of microorganisms such as yeast or prokaryotic cells. In a particular preferred embodiment, such vectors are suitable for stable transformation of bacterial cells, for example to transcribe the nucleic acid molecule of the present invention. For example, the vector may be pUC18. In particular, WO2007/099133 discloses vectors expressing fusion proteins based on DCC, such as the vectors identified as 7800 and 7809 in Example 1 of WO2007/099133. The present invention thus provides for a vector encoding the fusion protein of SEQ ID NO: 2, 3 or 4 in WO2012025618, or for a vector the DNA sequence SEQ ID NO: 1 in WO2012025618, for the DCC fusion protein.

The present invention also provides for a vector such as pUC18 containing a nucleic acid molecule of the present invention coding for a fusion protein as described and provided herein. As far as it concerns UNC5, the present invention therefore relates to a vector such a pUC18 containing a nucleic acid molecule encoding the amino acids 20-217 and 220-446 of SEQ ID NO: 1 fused together, or the sequence SEQ ID NO:1; the amino acids 20-215 and 218-444 of SEQ ID NO: 2 fused together, or the sequence SEQ ID NO: 2; the amino acids 20-217 and 220-446 of SEQ ID NO: 3 fused together, or the sequence SEQ ID NO:3; or the amino acids 20-217 and 220-446 of SEQ ID NO: 4 fused together, or the sequence SEQ ID NO:4. Particularly, the present invention provides for a vector such as pUC18 containing a nucleic acid molecule comprising the nucleotide sequence 73-666 of SEQ ID NO: 5, or 73-660 of SEQ ID NO: 6, or 73-666 of SEQ ID NO: 7 or 73-666 of SEQ ID NO: 8. These vectors also comprise the nucleotide sequence of SEQ ID NO: 9, particularly nucleotides 7-693. Generally, the vector may be capable of expressing said nucleic acid molecule in a eukaryotic host cell.

The vector as provided is an expression vector. Generally, expression vectors have been widely described in the literature. The expression vector may contain a selection marker gene and a replication-origin ensuring replication in the host. The expression vector may comprise a promoter. He may further comprise a termination signal for transcription. Between, the promoter and the termination signal there is preferably at least one restriction site or a polylinker which enables the insertion of a nucleic acid sequence/molecule desired to be expressed. In an embodiment, the vector is capable of expressing the protein in vivo, say the vector, once administered to a patient, is capable of expressing the protein in situ.

It is be understood that when the vector provided herein is generated by taking advantage of an expression vector known in the prior art that already comprises a promoter suitable to be employed in context of this invention, for example expression of a UNC5-fusion protein as described herein, the nucleic acid molecule is inserted into that vector in a manner that the resulting vector comprises preferably only one promoter suitable to be employed in context of this invention. The promoter may generally be heterologous or homologous. The vector described herein may also encompass more than one promoter, each respective promoter may be heterologous or homologous. The skilled person knows how such insertion can be put into practice. For example, the promoter can be excised either from the nucleic acid construct or from the expression vector prior to ligation.

The proteins according to the invention are preferably produced by recombinant means. Preferably, the protein expression is in eukaryotic cell with subsequent isolation of the polypeptide and usually purification to a pharmaceutically acceptable purity. For the protein expression, nucleic acids encoding the protein thereof are inserted into expression vectors by standard methods. Expression is performed in appropriate stable eukaryotic host cells like CHO cells, NS0 cells, SP2/0 cells, HEK293 cells, COS cells, and the protein is recovered from the cells (supernatant or cells after lysis). HEK293 cells appeared to be very suitable for this aim and forms a particular embodiment.

In an embodiment, the nucleic acid molecule of the present invention and/or the vector into which the polynucleotide described herein is cloned may be transduced, transformed or transfected or otherwise introduced into a host cell. For example, the host cell is a eukaryotic or a prokaryotic cell, preferably a eukaryotic cell. As a non-limiting example, the host cell is a mammalian cell. The host cell described herein is intended to be particularly useful for generating the UNC5-fusion proteins described and provided in the present invention.

Generally, the host cell described hereinabove may be a prokaryotic or eukaryotic cell, preferably a eukaryotic cell, comprising a nucleic acid molecule provided in the present invention or the vector described herein or a cell derived from such a cell and containing the nucleic acid molecule or the vector described herein. In a preferred embodiment, the host cell comprises, i.e. is genetically modified with the nucleic acid molecule of the present invention or the vector described herein in such a way that it contains the nucleic acid molecule of the present invention integrated into the genome. For example, such host cell described herein may be a human, yeast, or fungus cell. In one particular aspect, the host cell is capable to transcribe the nucleic acid molecule of the present invention. An overview of examples of different corresponding expression systems to be used for generating the host cell described herein is for instance contained in Methods in Enzymology 153 (1987), 385-516, in Bitter (Methods in Enzymology 153 (1987), 516-544), in Sawers (Applied Microbiology and Biotechnology 46 (1996), Billman-Jacobe (Current Opinion in Biotechnology 7 (1996), 500-4), Hockney (Trends in Biotechnology 12 (1994), 456-463), and in Griffiths (Methods in Molecular Biology 75 (1997), 427-440). The transformation or genetically engineering of the host cell with a nucleic acid molecule of the present invention or vector described herein can be carried out by standard methods, as for instance described in Sambrook and Russell (2001), Molecular Cloning: A Laboratory Manual, CHS Press, Cold Spring Harbor, N.Y. USA; Methods in Yeast Genetics, A Laboratory Course Manual, Cold Spring Harbor Laboratory Press, 1990.

The host cell comprising the nucleic acid molecule provided herein or a vector described herein may be a HEK293 cell or a HEK293-Freestyle cell (Human embryonic kidney cell line 293, Invitrogen). The present invention thus provides for a method for producing the DCC and UNC5-fusion proteins as provided and described herein. This method comprises the steps of expressing a nucleic acid molecule as provided and described herein in a suitable host cell, especially as described herein, and recovering the DCC or UNC5-fusion protein from said cell or the cell culture supernatant.

The present invention relates to compositions comprising a netrin-1 interfering drug. It relates in particular to compositions comprising a DCC and/or UNC5-fusion protein as provided herein or an in vivo expressing vector encoding a DCC and/or UNC5-fusion protein. It also relates in particular to compositions comprising an anti-netrin 1 antibody. These compositions may further comprise a pharmaceutically acceptable carrier, excipient and/or diluent. These compositions may be used as a pharmaceutical co-ingredient or a pharmaceutical and form a pharmaceutical composition or a medicament, to be used in combination with the chemotherapeutic drug or treatment on the same patient.

In an embodiment, both the DCC and/or UNC5-fusion proteins as provided herein or an in vivo expressing vector encoding a DCC and/or UNC5-fusion protein and the chemotherapeutic drug are within the same composition with a pharmaceutically acceptable carrier, excipient and/or diluent.

In another embodiment, they are presented under separate pharmaceutical forms. This form a composition or kit of parts comprising a chemotherapeutic drug and a netrin-1 interfering drug, for a simultaneous, separate or sequential administration to a patient.

In an embodiment of the method of treatment, use and compositions for use, the administration is sequential. In a preferred embodiment, the chemotherapeutic drug is administered first, and the netrin-1 interfering drug after. The interval between both administrations may be at least 5, 10, 15, 20 or 24 hours, preferably between 24 and 96 hours, more preferably between 24 and 72 hours, especially between 24 and 48 hours, for example 24 hours. In an embodiment, the netrin-1 interfering drug is simply administered the day after the administration of the chemotherapeutic drug.

These different pharmaceutical forms may be used in the methods of treatment of the invention, in sufficient amounts.

Examples of suitable pharmaceutical carriers are well known in the art. They include phosphate buffered saline solutions, water, emulsions, such as oil/water emulsions, various types of wetting agents, sterile solutions etc. Pharmaceutical compositions comprising such carriers can be formulated by well known conventional methods.

These pharmaceutical compositions can be administered to a subject at a suitable dose, i.e. for the netrin-1 interfering drug at least 1 mg/kg body weight, e.g. about 10 mg/kg body weight to about 100 mg/kg weight of the subject in which cancer, is to be treated. The chemotherapeutic drug may be administered at the usual dose, or at a reduced dose with respect to the usual dose as far as the combination has a synergic efficacy. For example the dose of chemotherapeutic drug is reduced by 10, 20, 30, 40, 50%, or more. Administration of the composition may be effected or administered by different ways, e.g. orally, (e.g. pill, tablet, buccal, sublingual, disintegrating, capsule, thin film, liquid solution or suspension, powder, solid crystals or liquid), rectally (e.g. suppository, enema) via injection (e.g. intravenously, subcutaneously, intramuscularly, intraperitoneally, intradermally) via inhalation (e.g., intrabronchially), topically, vaginally, epicutaneously or intranasally). The dosage regimen will be determined by the attending physician and clinical factors. As it well known in the medical arts, dosages for any one of patient depends upon many factors, including the patient's size, body surface area, age, the particular compound to be administered, sex time and route of administration, general health, and other drugs being administered concurrently.

The compositions and pharmaceutical compositions of the invention may be administered locally or systemically. Administration will preferably be intravenously or subcutaneously. The compositions and pharmaceutical compositions may also be administered directly to the target site, e.g. by biolistic delivery to an internal or external target site or by catheter to a site in an artery.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based in Ringer's dextrose), and the like. Preservatives and others additives may also be present such as, for example, antimicrobials, anti-oxidants, chelating agents, and inert gases and the like. Furthermore, also doses below or above of the exemplary ranges described hereinabove are envisioned, especially considering the aforementioned factors.

As already mentioned, the present invention relates to pharmaceutical compositions for use in treating a cancer overexpressing netrin-1.

Some embodiments of cancers include metastatic breast cancer, non-small cell lung cancer, aggressive neuroblastoma, pancreatic adenocarcinoma, primary melanoma (n=7), melanoma metastasis (n=6), ovarian cancers, glioblastoma, acute myeloid leukemia, chronic lymphocytic leukemia, aggressive B-cell lymphoma, sarcoma, renal adenocarcinoma, head and neck cancers, Testicular cancers (e.g. embryonal carcinoma, teratoma, yolk sac tumors), kidney cancers, stomach cancers, uterus cancers. Examples of cancers are listed infra.

Methods of determining whether a given cell expresses dependence receptors DCC and/or UNC5 on the surface and/or shows significant up-regulation of netrin-1 gene expression are well known in the art and comprise, but are not limited to, IHC (Immunohistochemistry) of FACS (Fluorescence activated cell sorting), quantitative PCR (e.g. with hexamer primed cDNA) or alternatively Western Blot paired with chromogenic dye-based protein detection techniques (such as silver or coomassie blue staining) or fluorescence- and luminescence-based detection methods for proteins in solutions and on gels, blots and microarrays, such as immunostaining, as well as immunoprecipitation, ELISA, microarrays, and mass spectrometry. In the context of the present invention, examples for cancers to be treated are listed herein including refractory versions of any of the mentioned cancers.

The invention will now be described with further details, in a non limiting way, by reference to the drawing in which:

FIGS. 1-4: Netrin-1 and its dependence receptors are up-regulated upon Doxorubicin treatment.

FIG. 1: Lung cancer cell lines A549 and H460 were treated with 2 µM Doxorubicin for 24 hours and Netrin-1 gene expression, normalized with Glyceraldehyde 3-phosphate dehydrogenase (GAPDH) and compared to not-treated cells, was evaluated by quantitative PCR. Doxorubicin treatment induced in both cell lines a strong induction of Netrin-1 gene expression. Results represent mean values of five independent experiments. Mann-Whitney tests were performed, and P value is indicated. DoxoR, Doxorubicin; Act. D, Actinomycin D; NT, not treated.

Figure 2:
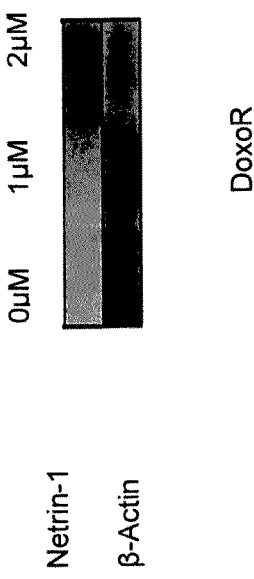

FIG. 2: A549 cells were treated with 1 µM and 2 µM Doxorubicin for 48 hours and Netrin-1 protein levels were evaluated by western blotting. Netrin-1 protein, normalized to β-actin, was strongly accumulated following Doxorubicin treatment.

Netrin-1 up-regulation was confirmed by immunofluorescence staining, following treatment with 2 µM Doxorubicin for 48 hours. Nuclei were counterstained with Hoescht staining (in blue). (Not shown)

Figure 3:
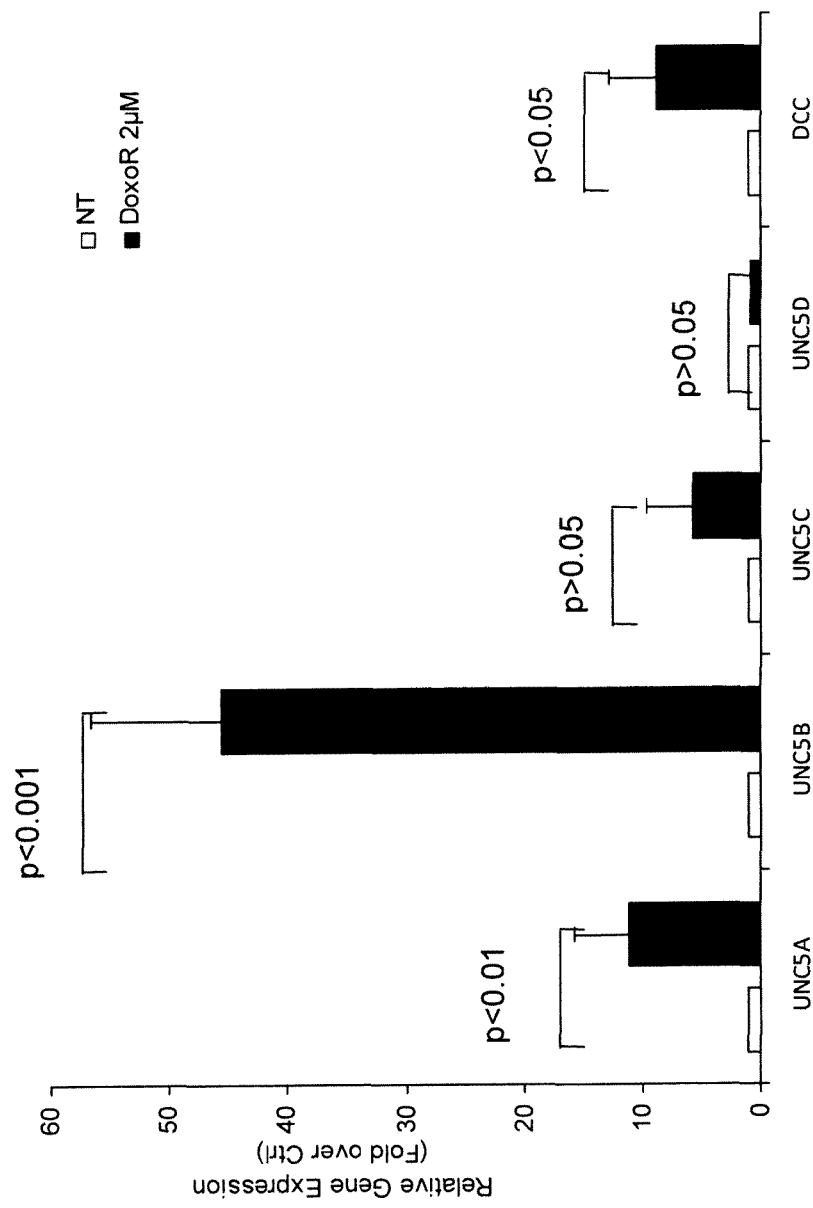

FIG. 3: Netrin-1 receptors gene expression was measured in A549 cells following Doxorubicin treatment. UNC5A, UNC5B and DCC gene expression was significantly up-regulated by Doxorubicin, while UNC5C and UNC5D showed non-significant variations. Mann-Whitney tests were performed, and P value is indicated. DoxoR, Doxorubicin; Act. D, Actinomycin D; NT, not treated.

Figure 4:
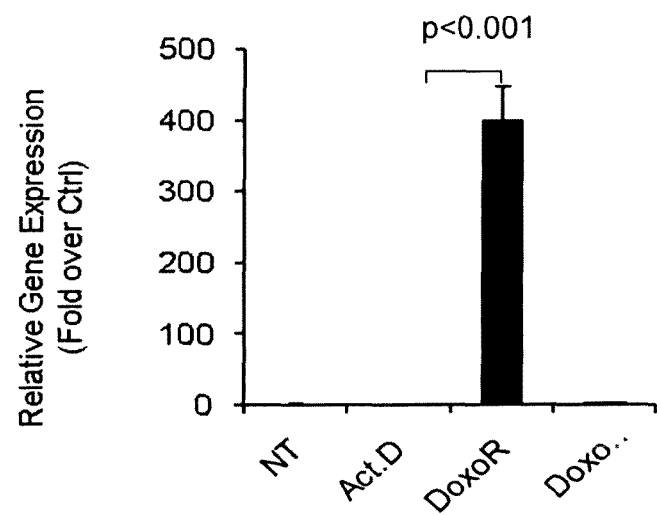

FIG. 4: Doxorubicin-induced Netrin-1 up-regulation is directly dependent by gene transcription. A549 cells were treated with 2 µM Doxorubicin and with the potent RNA polymerases inhibitor Actinomycin D (100 µg/ml) for 24 hours. Actinomycin D strongly inhibited Netrin-1 up-regulation following Doxorubicin treatment (Doxo.). Mann-Whitney tests were performed, and P value is indicated. DoxoR, Doxorubicin; Act. D, Actinomycin D; NT, not treated, Doxo., Doxorubicin+Actinomycin D.

FIGS. 5-9: Netrin-1 and its receptors expression is increased in several cancer cell lines and in ovarian tumors upon treatment with cytotoxic drugs.

FIGS. 5-8: Expression levels of Netrin-1 (NTN1), DCC, UNC5B and UNC5D were measured by quantitative RT-PCR. Breast cancer (HBL100), lung cancer (A549, H322, H358), colon cancer (HCT116, HCT8), pancreas cancer (MiaPacA-2, Panc-1), neuroblastoma (SH-Sy5y, IMR32), glioblastoma (SF767, U87MG) and ovary cancer (PA-1, TOV-112D, NIH-OVCAR3) cell lines were treated with classical chemotherapeutic drugs (Doxorubicin, Cisplatin, 5-Fluorouracil and Taxol), at different drugs concentration dependent on $IC_{50}$ values calculated for each cell line and drug treatment for 24 hours. Netrin-1 and its receptors gene expression was compared to control, not-treated cells, and variations was scored as following: −, no changes or down-regulation; +, between 2 and 4 fold over control of gene expression; ++, between 4 and 100 fold over control; +++, more than 100 fold over control; n.d., not determined; n.e., not expressed. Positive cell lines were determined for gene expression variations more than 2 fold over control. Gray boxes represent resistant (i.e., more than 50% cell survival after treatment with maximal drugs concentrations) cancer cell lines.

Figure 9:
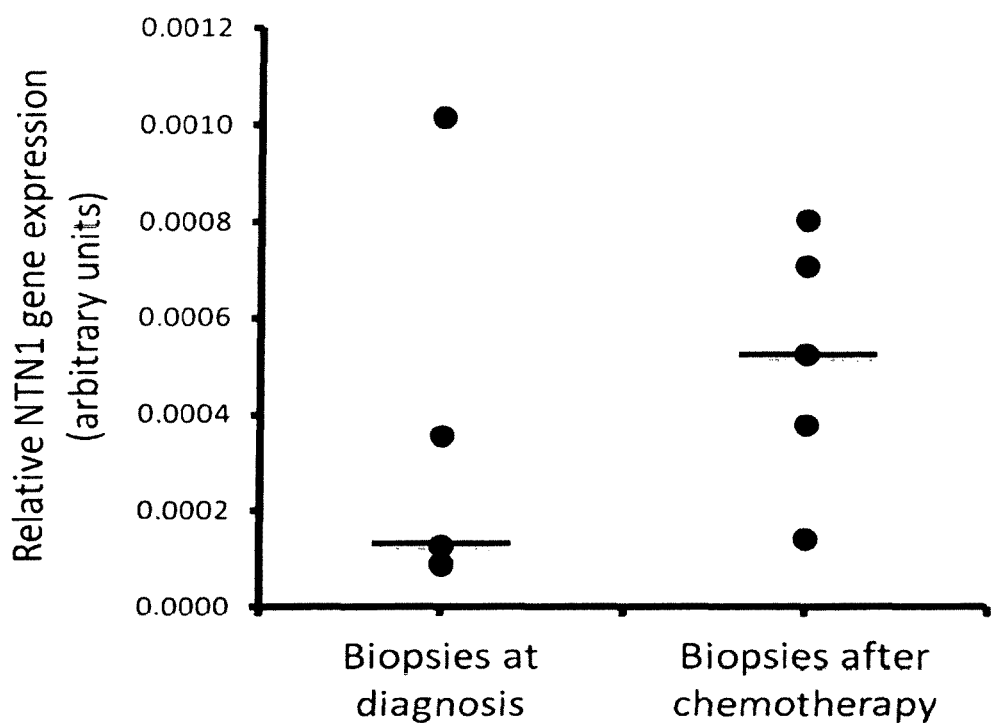

FIG. 9: Netrin-1 is over-expressed in ovarian tumor patients after chemotherapeutic treatment. Netrin-1 level, normalized with GAPDH, used as housekeeping gene, was analyzed in RNA extracted from ovarian biopsies of tumors from patients obtained before and after a chemotherapeutic cycle of carboplatin/taxol treatment. The median level of netrin-1 was calculated for each group.

FIGS. 10-15: Netrin-1 silencing sensitizes A549 cells to Doxorubicin and induces apoptotic cell death via UNC5B receptor.

Figure 11:
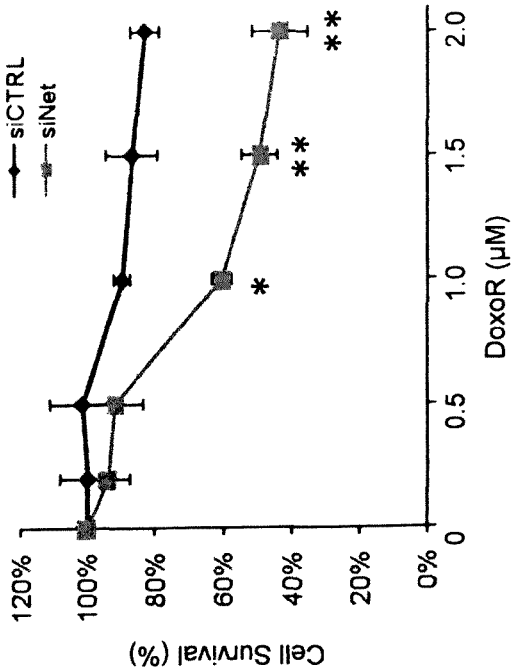
Figure 10:
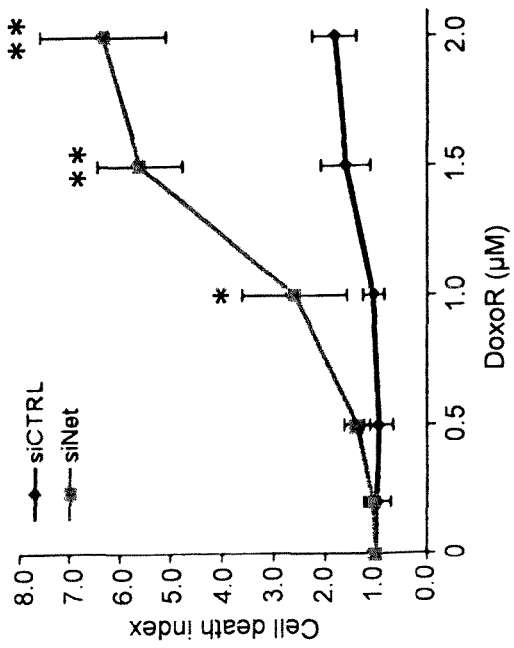

FIG. 10-12: Netrin-1 silencing sensitizes tumor cells to Doxorubicin. A549 cells were transfected with either a scramble siRNA (siCTRL, siRNA Universal Negative Control #1, Sigma-Aldrich) or with a specific siRNA targeting netrin-1 (siNet, sequence SEQ ID NO: 10: AAGCUG-GACGCAGCAUGAUGC). 24 hours after transfection, cells were treated with increasing concentrations of Doxorubicin. Cell death rate (FIG. 10), measured by toxilight kit as described in materials and methods section, and cell survival (FIG. 11), was evaluated 48 hours after treatment. Results were normalized to control, untreated cells. While scramble siRNA-transfected cells showed a general resistance to Doxorubicin treatment, netrin-1 silencing strongly induced cell death and decreased cell survival in presence of Doxorubicin. Evaluation of cell death percentage (FIG. 12), measured by 4',6-diamidino-2-phenylindole (DAPI) exclusion as described in the materials and methods section, confirmed that Netrin-1 siRNA sensitized A549 cells to 0.5 µM and 2 µM Doxorubicin treatment. *, P<0.05; **, P<0.01. DoxoR, Doxorubicin.

FIGS. 13-14: Netrin-1 silencing triggers apoptosis in combination with Doxorubicin treatment. A549 cells were transfected as in (FIGS. 10-12), and treated with the indicated Doxorubicin concentrations for 24 hours. Active caspase-3 (FIG. 13), normalized to untreated cells, and DNA fragmentation (FIG. 14) were evaluated as described in the materials and methods section. While Doxorubicin failed to induce apoptosis in A549 cells transfected with a scramble siRNA (siCTRL), cells silenced for netrin-1 showed a strong increase in the apoptotic rate. *, P<0.05; **, P<0.01. DoxoR, Doxorubicin.

FIG. 15: Combination of netrin-1 silencing and Doxorubicin treatment induces cell death through netrin-1 receptor UNC5B. A549 cells were transfected with scramble siRNA (siCTRL), netrin-1-specific siRNA (siNet), UNC5B-specific siRNA (siUnc5B) and with a combination of netrin-1 and UNC5B-targeting siRNA. 24 hours after transfection, cells were treated with the indicated Doxorubicin concentrations for 48 hours, and cell death rate was measured by toxilight and normalized to control, untreated cells. While netrin-1 silencing (siNet) sensitized A549 cells to Doxorubicin treatment, as compared to siCTRL-transfected cells, the simultaneously silencing of netrin-1 and UNC5B (siNet+siUnc5B) rescued cell death induction by siNet and Doxorubicin treatment. *, P<0.05; **, P<0.01. DoxoR, Doxorubicin.

FIGS. 16-21: Interference to netrin-1 and its receptors interaction sensitizes tumor cells to cytotoxic drugs.

Figure 16:
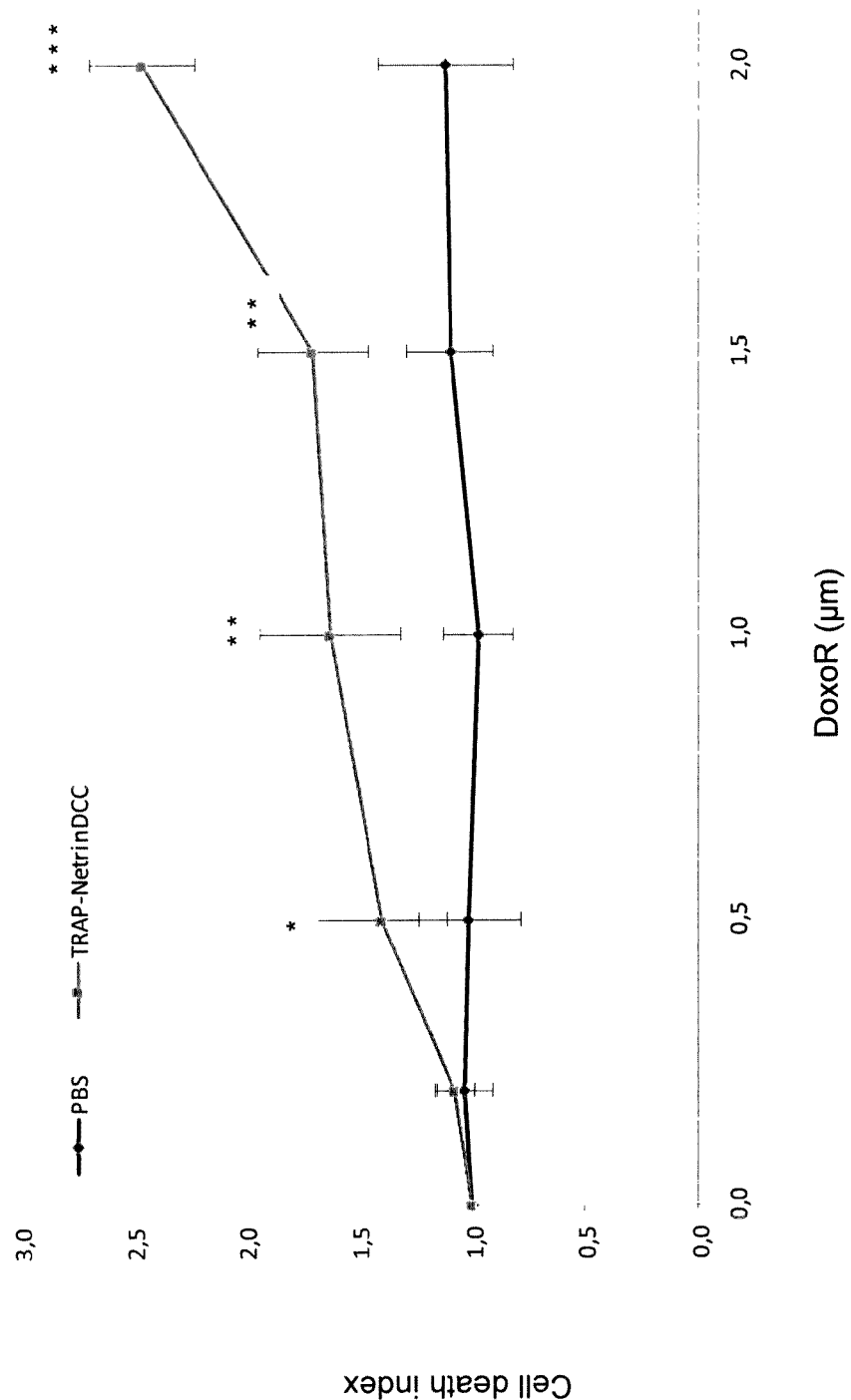
Figure 17:
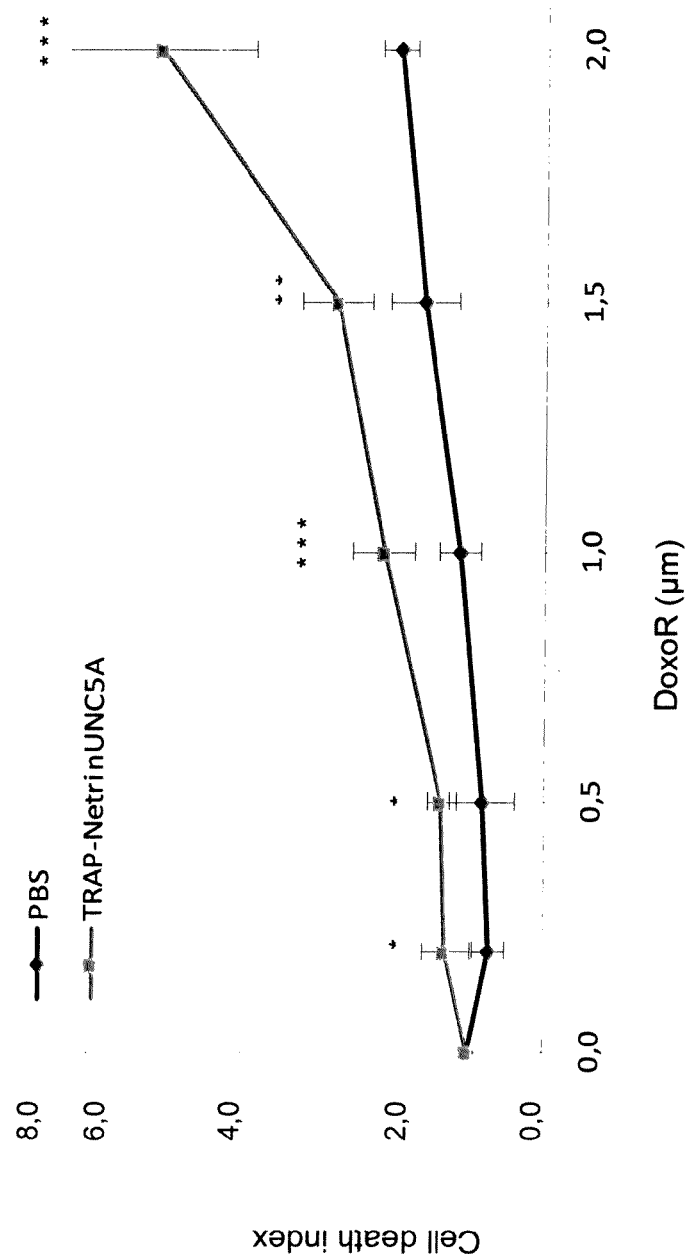

FIGS. 16-17: A549 cells were treated for 48 hours with the indicated Doxorubicin concentrations in presence or not of 2 µg/mL TRAP-netrin$^{DCC}$ (FIG. 16) and TRAP-netrin$^{Unc5A}$ (FIG. 17). The co-treatment with Doxorubicin and the two recombinant fusion proteins, increased cell death rate, measured by toxilight, as compared to Doxorubicin- and PBS-treated cells. Results were normalized to untreated cells. *, P<0.05; , P<0.01; *, P<0.001. DoxoR, Doxorubicin.

Figure 18:
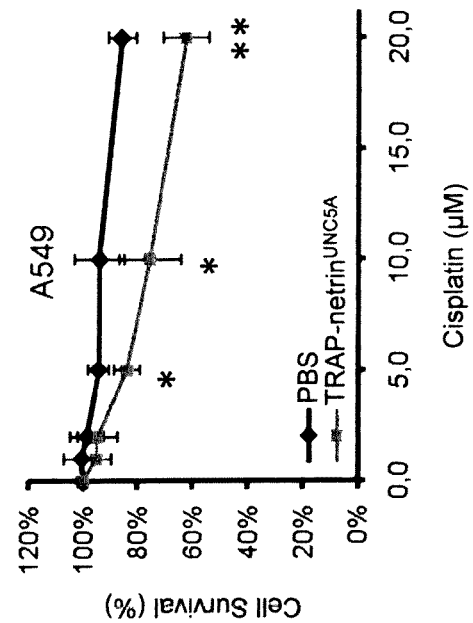
Figure 19:
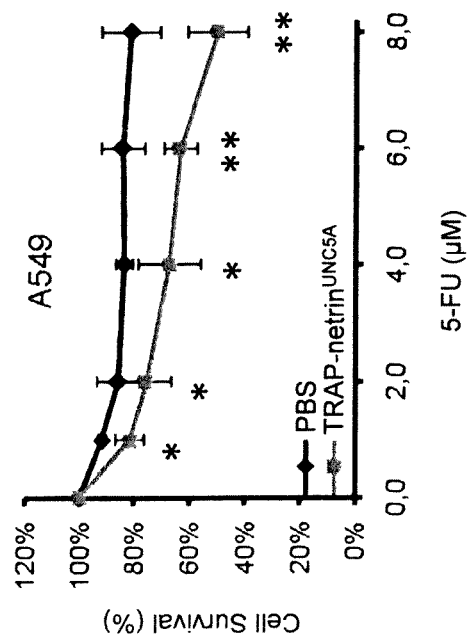

FIGS. 18-19: A549 cells were treated with PBS or 2 µg/mL TRAP-netrin$^{Unc5A}$, in presence of the indicated concentrations of 5-Fluorouracil (5-FU, FIG. 18) or Cisplatin (FIG. 19). 48 hours after co-treatment, cell survival was measured by MTS and normalized to untreated cells. *, P<0.05; , P<0.01; *, P<0.001. DoxoR, Doxorubicin.

Figure 21:
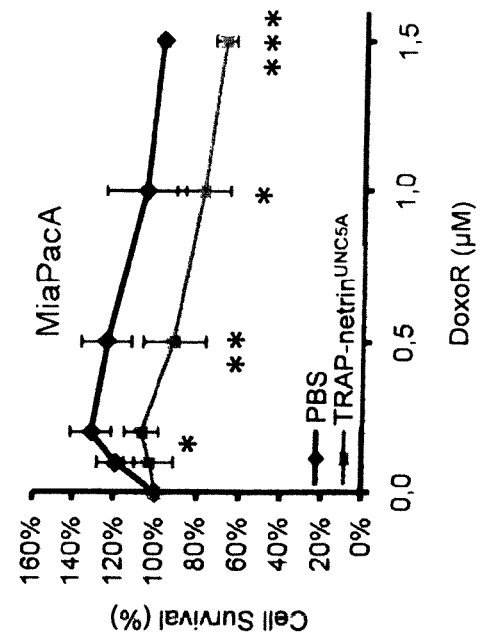
Figure 20:
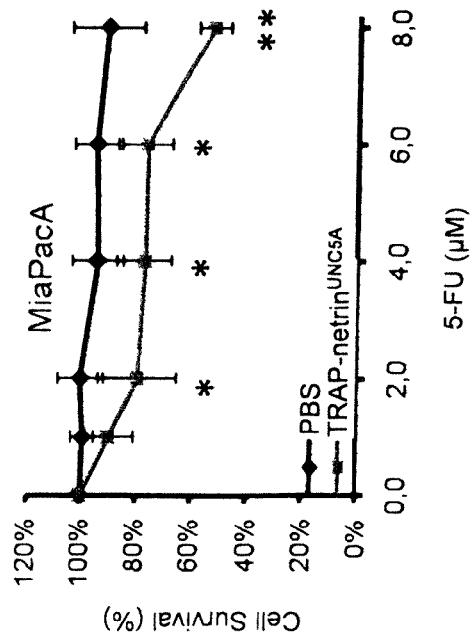

FIGS. 20-21: MiaPacA cells were treated with PBS or 2 µg/mL TRAP-netrin$^{Unc5A}$, in presence of the indicated concentrations of 5-FU (FIG. 20) or Doxorubicin (FIG. 21). 48 hours after co-treatment, cell survival was measured by MTS and normalized to untreated cells. *, P<0.05; **, P<0.01; P<0.001. DoxoR, Doxorubicin.

Figure 22:
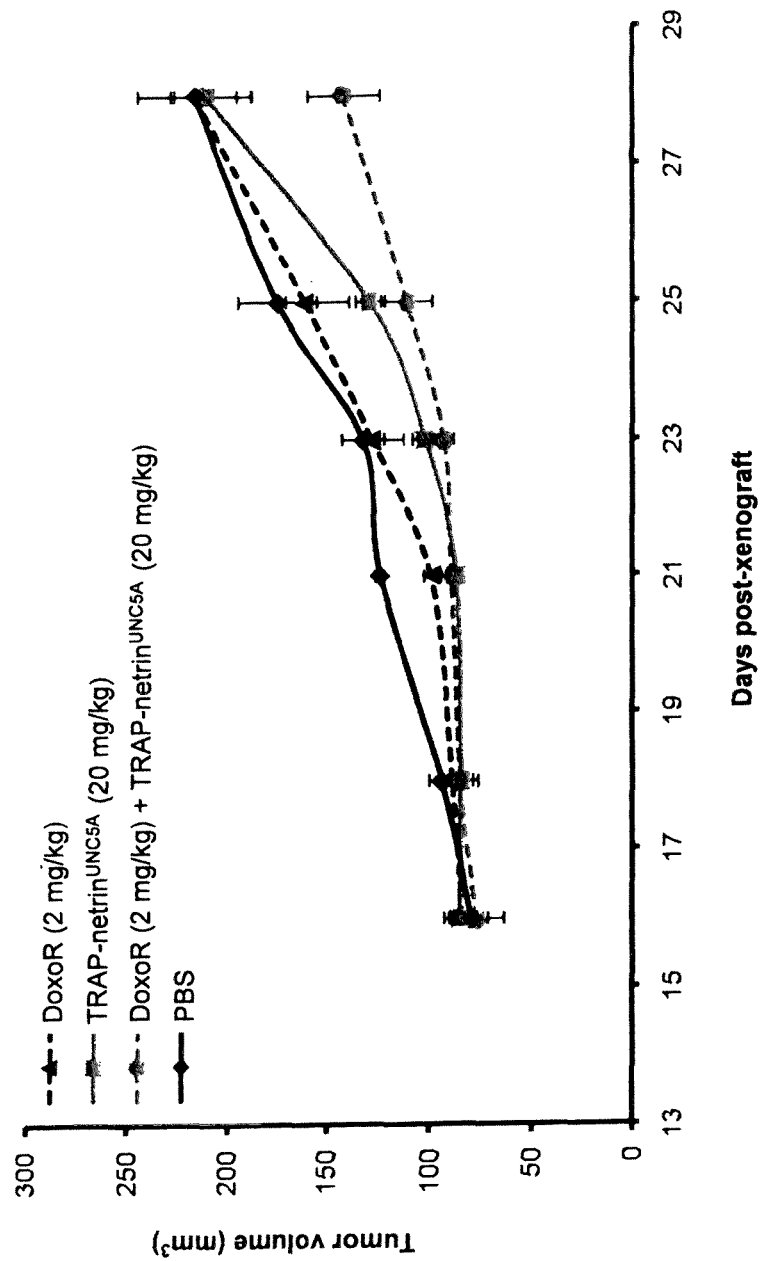

FIG. 22: Netrin-1 interfering potentiates Doxorubicin anti-cancer effect in a preclinical animal model. A549 cells were engrafted in seven-weeks old female athymic nude mice. Once tumors reached a 100 mm³-volume, mice were treated intraperitoneally with TRAP-netrin$^{UNC5A}$ (20 mg/kg), Doxorubicin (2 mg/kg) or with a combination of both drugs, twice a week for two weeks. As a control, mice were injected with PBS. Histogram represents tumor volume growth for each group as a function of days post-xenografts. While both drug alone was not able to reduce tumor growth, combination of TRAP-netrin$^{UNC5A}$ and Doxorubicin treatment significantly reduced tumor growth.

FIGS. 23-27—Netrin-1 receptors gene expression following cytotoxic drugs treatment.

FIGS. 23-24: Cancer cells were treated as described in FIG. 5, and UNC5A and UNC5C gene expression was evaluated after drugs treatment. Scoring system is the same used in FIG. 5. Both receptors showed poor expression levels changes after treatment, as compared to untreated cells.

FIGS. 25-27: Netrin-1 receptors expression levels in ovarian biopsies of tumors from patients before and after carboplatin/taxol treatment. The median values were calculated from each group. UNC5B (FIG. 25), UNC5D (C=FIG. 26) and DCC (FIG. 27) gene expression showed a similar up-regulation after chemo-therapeutic treatment. Gene expression levels were normalized to Glyceraldehyde 3-phosphate dehydrogenase (GAPDH), used as housekeeping gene.

FIG. 28: Cell sensitivity to cytotoxic drugs. The inhibitory concentration (IC) $IC_{10}$, $IC_{30}$ and $IC_{50}$ in response to Cisplatin, 5-Fluoruracil (5FU), Doxorubicin, and paclitaxel (Taxol) was determined for the indicated cell lines by MTS assays. $IC_{50}$ values were calculated by linear regression of double reciprocal plots. For resistant cancer cell lines (i.e., more than 50% cell survival after treatment with maximal drugs concentrations $IC_{MAX}$), represented by gray boxes, $IC_{MAX}$ and fractions were calculated.

Figure 29:
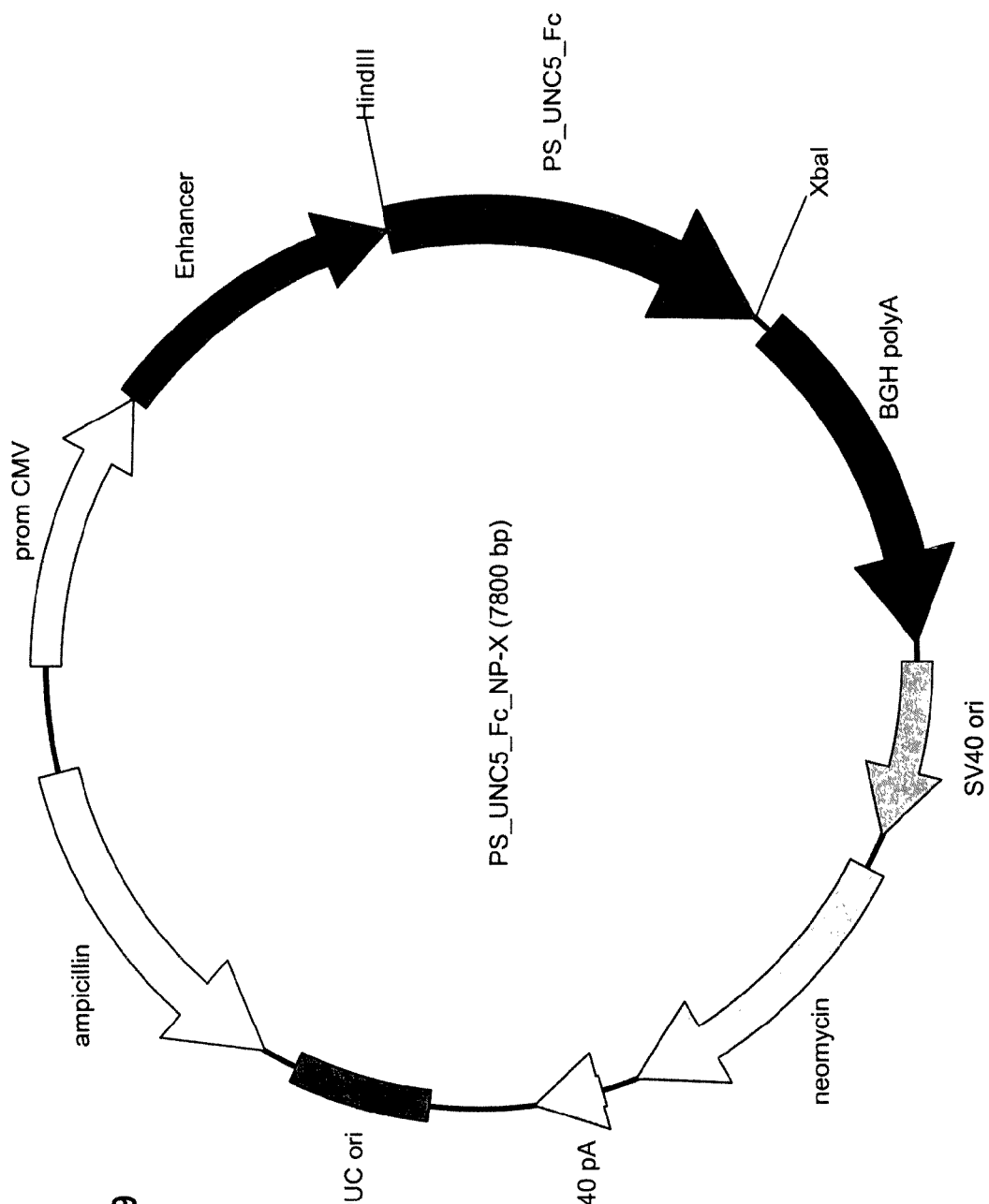

FIG. 29: Map of expression plasmid NP-X.

SEQUENCE LISTING

| SEQ ID NO: | Amino acid sequence | Nucleic acid sequence |
|---|---|---|
| 1 | UNC5A-TRAP with peptide signal | |
| 2 | UNC5B-TRAP with peptide signal | |
| 3 | UNC5C-TRAP with peptide signal | |
| 4 | UNC5D-TRAP with peptide signal | |
| 5 | | UNC5A |
| 6 | | UNC5B |
| 7 | | UNC5C |
| 8 | | UNC5D |
| 9 | | Human IgG1 Fc |
| 10 | | siRNA strand (sense) |
| 11 | | primer |
| 12 | | primer |
| 13 | Netrin-1 | |
| 14 | | Netrin-1 |

I. Materials and Methods:

1. Quantitative RT-PCR Allowing to Assess Netrin-1 Expression or Overexpression:

Total RNA was extracted using NucleoSpin® RNA II Kit (Macherey Nagel, Duren, Germany) according to manufacturer's protocol. RT-PCR reactions were performed with iScript® cDNA Synthesis Kit (Biorad). One mg total RNA was reverse-transcribed using the following program: 25° C. for 5 min, 42° C. for 30 min and 85° C. for 5 min. For expression studies, the target transcripts were amplified in LightCycler® 2.0 apparatus (Roche Applied Science), using the LightCycler FastStart DNA Master SYBR Green I Kit (Roche Applied Science). Expression of target genes was normalized to glyceraldehyde 3-phosphate dehydrogenase (GAPDH) and phosphoglycerate kinase (PGK) genes, used as housekeeping genes. The amount of target transcripts, normalized to the housekeeping gene, was calculated using the comparative $C_T$ method. A validation experiment was performed, in order to demonstrate that efficiencies of target and housekeeping genes were approximately equal. The sequences of the primers are as follows:
Forward primer: aaaagtactgcaagaaggactatgc SEQ ID NO:11.
Reverse primer: ccctgcttatacacggagatg SEQ ID NO:12.

2. Netrin-1 Protein Quantification in Human Cancer Cells:

For immunoblot analysis, cells were lysed by sonication in modified RIPA buffer (50 mM Tris-HCl, pH7.5, 150 mM NaCl, 1% NP-40, 0.5% sodium deoxycholate, 0.1% SDS, 1 mM EDTA, protease inhibitor cocktail and 5 mM DTT) and incubated 1 h at 4° C. Cellular debris were pelleted by centrifugation (10.000 g 15' at 4° C.) and protein extracts (200 µg per lane) were loaded onto 10% SDS-polyacrylamide gels and blotted onto PVDF sheets (Millipore Corporation, Billerica, Mass., U.S.A.). Filters were blocked with 10% non-fat dried milk and 5% BSA in PBS/0.1% Tween 20 (PBS-T) over-night and then incubated for 2 h with rabbit polyclonal α-netrin-1 (dilution 1:500, clone H104, Santa Cruz Biotechnology, Santa Cruz, Calif., USA) and mouse monoclonal β-actin (Santa Cruz Biotechnologies) antibodies. After three washes with PBS-T, filters were incubated with the appropriate HRP-conjugated secondary antibody (1:10000, Jackson ImmunoResearch, Suffolk, UK) for 1 h. Detection was performed using West Dura Chemiluminescence System (Pierce, Rockford, Ill., U.S.A.).

For immunofluorescence study, cells were detached, centrifuged on cover slips with a cytospiner (Shandon Cytospin 3, Thermo Scientific) and fixed for 30 minutes with 4% (v/v) paraformaldehyde. Cells were then permeabilized for 30 minutes in 0.2% Triton X-100/PBS and blocked in PBS containing 2% BSA and 2% normal donkey serum. Endogenous netrin-1 was stained using rat monoclonal α-netrin-1 antibody (R&D systems) and Alexa-488 Donkey anti-rat IgG (Molecular probes). Nuclei were counterstained using Hoescht staining (Sigma).

3. Cell Death Assay and Conventional Drugs Treatment:

Cell death was evaluated by means of different methods. For total cell death assays, $5*10^3$ cells per well were grown in 96-well plate in serum-poor medium and treated with Doxorubicin. 48 hours later, cell death was evaluated using the bioluminescent cytotoxicity assay ToxiLight (Lonza, Basel, Switzerland), according to manufacturer's instruction. Alternatively, cell death percentage was measured by acridine orange and DAPI staining, using the NucleoCounter NC-3000 system (ChemoMetec NS, Allerød, Denmark). Briefly, $5*10^4$ cells were plated in 12-well plate and treated with Doxorubicin. 48 hours after treatment, floating and adherent cells were collected, suspended in PBS and mixed with two different dyes, acridine orange, staining the entire population of cells, and 4',6-diamidino-2-phenylindole (DAPI), staining the non-viable cells. Cell death rate, measured as DAPI-positive cells in total cell population, was then determined by NucleoCounter NC-3000, following the manufacture's application note. Cell survival was measured by MTS assay (CellTiter 96 AQueous One Solution Cell Proliferation Assay, Promega) in 96-well plates. MTS assay was performed according to the manufacturer's procedures on $3*10^3$ cells grown in serum-poor medium for 16 hours and then treated for 48 hours with the indicated Doxorubicin concentrations in serum-free medium. Caspase-3 activity assay was performed as previously described (21) using the Caspase 3/CPP32 Fluorimetric Assay Kit (Gentaur Biovision, Brussel, Belgium), according to the manufacturer's instructions. Caspase activity (activity/min/microgram of protein) was calculated from a 1 h kinetic cycle reading on a spectrofluorimeter (405 nm/510 nm, Infinite F500, Tecan, Männedorf, Switzerland).

4. Candidate Drugs:

TRAP-netrin$^{DCC}$ and TRAP-netrin$^{UNC5A}$ are respectively the fifth fibronectin domain of DCC ectodomain and the two immunoglobin (Ig1-Ig2) domains of the UNC5A ectodomain, fused to IgG1 Fc portion. These two recombinant proteins were produced respectively in 293-free-style and CHO-free-style.

TRAP-netrin$^{DCC}$ has been produced according to examples 1-4 of WO2012025618 using plasmid 7800. A similar fusion protein may be produced using vector 7809 also disclosed in these examples of WO2012025618.

TRAP-netrin$^{UNC5A}$ has been produced using the method described under 5.

5. Production of TRAP-netrin$^{UNC5A}$ (UNC5A-Fc), TRAP-netrin$^{UNC5B}$ (UNC5B-Fc) and TRAP-netrin$^{UNC5C}$ (UNC5C-Fc)

Plasmid Construction

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions. Desired gene segments were prepared by gene synthesis. The synthesized gene fragments were cloned into a specified expression vector. The DNA sequence of the subcloned gene fragments were confirmed by DNA sequencing.

Expression plasmid is represented on FIG. 11 and noted PS-UNC5-Fc-NP-X (PS for peptide signal, and X may be V-01 for UNC5A, V-02 for UNC5B and V-03 for UNC5C.

This vector is an expression plasmid e.g. for transient expression of an artificial Ig Fc fusion protein in which the Ig-like domains of the human UNC5A, B, or C receptor is fused to the hinge region of human IgG 1 antibody (Fc constant region; Hinge-CH2-CH3) with the introduction of a 2 amino acid artificial linker sequence.

Chemical gene synthesis was used to prepare the DNA segments of 672 (SEQ ID NO: 5, 7) or 676 bps (SEQ ID NO: 6) flanked by a unique HindIII and KpnI restriction endonuclease at the 5'- and the 3'-end, respectively. Similarly, was prepared the DNA segment of 699 bps (SEQ ID NO: 9) flanked by a unique KpnI and XbaI restriction endonuclease at the 5'- and the 3'-end, respectively. A DNA segment coding for the open reading frame (ORF) of the desired UNC5-fusion protein (UNC5-Fc fusion protein) (SEQ ID NO: 1, 2, 3) with the Kappa 2 signal peptide at the N-terminal position was obtained by ligation of the two DNA segments cited above. The gene was introduced in an expression vector (NP-V) to the immediate promoter of CMV-IE and enhancer hE1 and the bovine growth hormone (bGH) polyadenylation site.

The UNC5-fusion protein (UNC5-Fusion protein) is composed of a murine signal sequence (amino acids 1 to 19 of SEQ ID NO: 1, 2 or 3), the two immunoglobulin-like domains of the human UNC5 receptor (UNC5A: amino acids 20 to 217 of SEQ ID NO: 1; correspond to amino acids 34 to 240 of UNC5A of amino acid sequence UniProt ID: Q6ZN44; UNC5B: amino acids 20 to 215 of SEQ ID NO: 2; correspond to amino acids 49 to 244 of UNC5B of amino acid sequence UniProt ID: Q8IZJ1; UNC5C: amino acids 20 to 217 of SEQ ID NO: 3; correspond to amino acids 61 to 258 of UNC5C of amino acid sequence UniProt ID: O95185; two amino acid linker (from cloning site; amino acids 199 to 200 of SEQ ID NO: 3) and the human IgGI antibody Fc constant region (amino acids 220 to 446 of SEQ ID NO: 1 or 3; amino acids 218 to 444 of SEQ ID NO: 2). The mature UNC5-Fc fusion proteins lack the signal peptide.

Transient Transfection, Expression and Purification

Recombinant proteins were obtained by transient transfection of Freestyle HEK 293 cells (Invitrogen) growing in suspension in 293 Freestyle culture medium (Invitrogen) with 8% $CO_2$ at 37° C. For transfection 293Fectin® reagent (Invitrogen) was used according to manufacturer's instructions. Three days after transfection, supernatants were harvested and clarified by centrifugation (10 min at 200 g). The Fc-fusion proteins were purified using Protein G Sepharose 4 FF according to the manufacturer's instructions. Elutions were performed in 0.1M Glycin pH 2.8. Eluates were neutralized in 1M Tris-Hcl pH 9.0 and dialyzed over night against PBS. Final analytics were performed using polyacrylamide gel electrophoresis in denaturing and non denaturing conditions followed by coomassie blue staining or by western blot analysis after nitrocellulose transfer (using an anti-human IgG (Fc specific)-HRP antibody, Sigma).

Recombinant UNC5A-Fc as obtained by transient transfection of Freestyle CHO-S cells (Chine Hamster Ovary, Invitrogen) growing in suspension in a chemically defined, animal-component free, serum-free media with 8% $CO_2$ at 31° C. For transfection FreeStyle™ MAX Reagent (Invitrogen) was used according to manufacturer's instructions. The UNC5A-Fusion protein (SEQ ID NO: 1) could be secreted with high efficiency at a rate of at least 300 mg/L at transient expression in Freestyle CHO-S cells. Supernatant was harvested by centrifugation and sterile filtered (0.2 μm). The concentration of UNC5A-Fc in the supernatant was determined using the BioRad Experion system. The Fc-fusion protein was subsequently purified via cation exchange chromatography followed by Protein A affinity chromatography (PALL Protein A Ceramic Hyper D) according to manufacturer's instructions with the exception of elution in 0.1M Glycine HCl pH 3.0. The eluate was neutralized with 1M Tris-HCl pH 9 and dialyzed overnight against 20 mM Citrate, 134 mM NaCl, pH 6.2. Final analytics were performed with the Bio-Rad Experion system for quantification, size verification and presence of contaminants.

TABLE

Results of expression

| Plasmid # | Characteristic | Sequence | MW kDa | Expression yield μg/mL (Freestyle HEK 293 supernatant day 3) | Expression yield μg/mL (Freestyle CHO-S supernatant day 8) |
|---|---|---|---|---|---|
| NP-V-01 | UNC5A-Fc | SEQ ID NO. 1 | 48.17 | 3.5 | 300 |
| NP-V-02 | UNC5B-Fc | SEQ ID NO. 2 | 48.31 | 25 | — |
| NP-V-03 | UNC5C-Fc | SEQ ID NO. 3 | 48.55 | 5 | — |

In the following experiment, UNC5A-Fc produced in CHO-S cells has been used.

6. Animal Model:

Seven-week-old (20-22 g body weight) female athymic nu/nu mice were obtained from Charles River animal facility. The mice were housed in sterilized filter-topped cages and maintained in a pathogen-free animal facility. A549 cells were implanted by s.c. injection of $10^7$ cells in 200 μL of PBS into the right flank of the mice. Once tumors were established (V≈100 $mm^3$), mice were treated with netrin-1 interfering drugs and/or cytotoxic drugs for two weeks. Tumor sizes were measured with a caliper. The tumor volume was calculated with the formula v=0.5* (length*$width^2$). At the end of the treatment, tumors were harvested, weighted and were embedded in 7.5% gelatin— 0.12M sucrose and sectioned into 20 μm slices.

7. Statistical Analysis:

The data reported are the mean±S.D. of at least three independent determinations, each performed in triplicate. Statistical analysis was performed by the nonparametric Mann-Whitney U test unless indicated.

II. Results and Discussion

1. Netrin-1 and its Receptors are Up-regulated in Tumor Cells Upon Conventional Chemotherapies.

We first analyzed by quantitative RT-PCR the level of netrin-1 in two lung cancer cell lines A549 and H460 in response to Doxorubicin. As shown in FIG. 1, netrin-1 mRNA level was massively increased in both cell lines (respectively by 430 and 300 fold) upon treatment with 2 μM Doxorubicin. This increase of mRNA was associated with a robust increase of netrin-1 protein expression (FIG. 2 and immunofluorescence (not shown).

Next, we analyzed the level of the netrin-1 receptors DCC and UNC5H-UNC5A, UNC5B, UNC5C and UNC5D—in response to Doxorubicin. As shown in FIG. 3, levels of DCC, UNC5A, UNC5B and UNC5D increase concomitantly to netrin-1 levels, in A549 cells treated with Doxorubicin. This increase reached 44 folds for the UNC5B receptor. To monitor whether this up-regulation of netrin-1 and its receptors is related to increased gene transcription, A549 cells were treated with Doxorubicin in the presence of the RNA polymerase inhibitor Actinomycin D. As shown in FIG. 4, Actinomycin D fully prevents Doxorubicin-mediated netrin-1 up-regulation, thus supporting the view that conventional therapeutic drugs triggers increase of netrin-1 and its receptors via enhanced gene transcription.

To investigate whether netrin-1 and its receptors upregulation was restricted to Doxorubicin or was a general response to chemotherapeutic agents, netrin-1 levels were analyzed by quantitative RT-PCR in a panel of 15 cancer cell lines in response to various conventional chemotherapeutic drugs, such as Doxorubicin, 5-Fluoruracil (5FU), paclitaxel (Taxol) and Cisplatin. Analysis of netrin-1 level was performed upon treatment with 3 concentrations corresponding to the determined $IC_{10}$, $IC_{30}$ or $IC_{50}$ of each drug for each cell lines (FIG. 28). In cell lines which appeared to be resistant to specific drugs (FIG. 28), a concentration corresponding to maximal effective concentration ($IC_{MAX}$) was used to monitor netrin-1 level. As shown in FIG. 5-8, Doxorubicin and 5FU both trigger a significant (i.e., >2 fold over control) increase of netrin-1 in respectively 60% and 36% of cancer cell lines. Treatment with Taxol and Cisplatin was associated with netrin-1 up-regulation in only 20% and 21% of cell lines respectively. Netrin-1 up-regulation upon chemotherapeutic drugs treatment is not tumor type specific as netrin-1 up-regulation was seen in at least one cell line of breast, lung, pancreatic and ovarian cancers and as well as in neuroblastoma and glioblastoma cell lines. We could not detect any correlation between netrin-1 up-regulation and chemoresistance, as netrin-1 up-regulation was detected in both resistant and sensitive cell lines, and as some resistant cell lines did not show netrin-1 up-regulation (FIG. 5-8).

The expression of netrin-1 dependence receptors in response to these cytotoxic agents was also investigated in the 15 cancer cell lines (FIG. 5-8). Similarly to netrin-1 response, Doxorubicin seemed to have the largest effect, as it is associated with the up-regulation of DCC, UNC5B and UNC5D in, respectively, 87%, 80% and 67% of the cell lines screened. DCC, which displays an overall low expression in the screened cancer cell lines, is the netrin-1 receptor showing the largest spectrum of up-regulation as DCC expression was strongly increased in 36%, 43%, and 53% of cell lines in response to respectively Cisplatin, 5FU and Taxol. Levels of the netrin-1 receptors UNC5A and UNC5C remained largely unaffected by treatment with cytotoxic drugs in most of the cell lines that were screened (FIG. 23-24). Together, these data support the view that netrin-1 and its receptors up-regulation frequently occurs in response to conventional drugs treatment.

We finally analysed netrin-1 and receptors level in ovarian cancer specimens from patients before and after treatment with carboplatin/taxol. As shown in FIG. 9, netrin-1 mRNA was up-regulated after chemotherapy. Moreover, DCC, UNC5B and UNC5D level was also affected by carboplatin/taxol treatment (FIG. 25-27).

2. Netrin-1 Interference Potentiates Cytotoxic Drugs Induced Cell Death.

The fact that both netrin-1 and its receptors are up-regulated upon conventional drugs treatment suggests that the dependence for survival on netrin-1 is amplified in chemo-treated cancer cells. We thus first analysed Doxorubicin-induced cell death upon silencing of netrin-1 by a siRNA strategy. A549 cells were then transfected with a netrin-1 siRNA and treated with increasing concentration of Doxorubicin. Silencing of netrin-1 was associated with a marked potentiation of Doxorubicin-induced cell death as shown by measurement of loss of cell permeability (FIG. 10), cell survival (FIG. 11), DAPI exclusion (FIG. 12), caspase activation (FIG. 13) or DNA fragmentation (FIG. 14). To determine whether this increased sensitivity was due to the pro-apoptotic engagement of unbound netrin-1 dependence receptors, a similar experiment was performed in settings of silencing of UNC5B, the main netrin-1 receptor expressed upon Doxorubicin treatment in A549 cells. As shown in FIG. 15, silencing of UNC5B is associated with the inhibition of the potentiation of cell death induced by netrin-1 silencing and Doxorubicin treatment.

We thus looked at a possible similar potentiation effect using a more therapeutically relevant way for netrin-1 interference. Two drug candidates, TRAP-netric$^{DCC}$ and TRAP-netrin$^{UNC5A}$, which are Fc-stabilized ectodomains of respectively DCC or UNC5A, have been shown to trigger death of netrin-1 expressing tumor cells in vitro and tumor growth inhibition in engrafted mice models (not shown). As shown in FIG. 16-17, these two candidate drugs strongly potentiate Doxorubicin-induced cell death in A549 cells. As netrin-1 and receptors were also up-regulated upon 5FU and Cisplatin treatment (FIG. 5-8), we performed similar combination of TRAP-netrin$^{UNC5A}$ with 5FU and Cisplatin. Comparable potentiating effect on cell death was observed upon co-treatment with 5FU or Cisplatin and TRAP-netrin$^{UNC5A}$ (FIG. 18-19). Similarly, in pancreatic cancer cell line MiaPacA where 5FU and Doxorubicin have been shown to up-regulate netrin-1 and its receptors, co-treatment of 5FU or Doxorubicin and TRAP-netrin$^{UNC5A}$ potentiated cell death (FIG. 20-21).

3. Netrin-1 Interference Potentiates Cytotoxic Drugs Anti-Cancer Effect in a Preclinical Animal Model of Cancer.

We then assessed whether the in vitro effect seen above could be translated in vivo in a therapeutic perspective. A549 cells were engrafted in nude mice and animals with palpable tumors were treated twice a week by i.p. injection of vehicule or TRAP-netrin$^{UNC5A}$ at 20 mg/kg alone or in combination with 2 mg/kg of Doxorubicin. Single agent—TRAP-netrin$^{UNC5A}$ or Doxorubicin—treatment used upon these administration schemes and doses were associated with detectable but weak tumor growth inhibiting effect (FIG. 22). However, co-treatment of Doxorubicin and TRAP-netrin$^{UNC5A}$ was associated with a strong and prolonged inhibition of tumor growth. Taken together, these data support the view that combining netrin-1 interference based treatment with a conventional chemotherapy is associated with synergic anti-cancer effect.

4. To Combine Netrin-1 Interference and Cytotoxic Drugs is a Promising Therapeutic Approach.

We show here that, cancer cell lines up-regulate expression of netrin-1 in response to treatment with cytotoxic drugs, The cytotoxic drugs tested here, which include Doxorubicin, Cisplatin, 5FU, and paclitaxel (Taxol) are commonly used in the management of patients with non-small cell lung cancer, breast, colorectal and ovarian cancers both in the adjuvant and advanced setting. Moreover we have shown, using a so far restricted panel of human samples, that primary ovarian tumors from patients treated with Carboplatin/Taxol, display an increase in netrin-1 level compared to the same tumors before treatment. Even though in cell culture this netrin-1 up-regulation differs in kinetics and amplitude depending on the drug used and the cancer cell type (FIG. 1), the fact that these drugs are known to affect different cellular mechanisms support the view that netrin-1 up-regulation is rather a general survival stress response than a specific alteration of a specific pathway affected by a specific chemotherapeutic drug. It is then interesting to speculate that this netrin-1 up-regulation may be a survival mechanism employed by cancer cell in response to these drugs.

Although the mechanisms for this up-regulation of netrin-1 remain to be determined, it may have significant therapeutic consequences. Indeed netrin-1 interfering drugs are currently under preclinical development; combination of these compounds with conventional cytotoxic agents may prove synergistic. We have shown that netrin-1 expression is up-regulated in samples from breast, ovarian, pancreatic and non-small cell lung cancer patients and that interfering with the Netrin-1 autocrine/paracrine loop triggers apoptosis of cancer cells in several models. Furthermore, the data presented here suggests that an even larger subset of patient may benefit from Netrin-1 targeting agents, either alone or in combination with cytotoxic agents. Based on our in vivo observation on tumor bearing mice, the combination does not appear to increase toxicity compared to cytotoxic agents alone. The pre-clinical data showed here support the view that combining conventional drugs plus netrin-1 interference may lead to an increased efficacy with reduced concentration of conventional drugs. Together these data support the rationale of testing netrin-1 interference based therapy in early clinical trials in combination with conventional chemotherapies.

5. Example of Cancers Over-Expressing Netrin-1 and Expressing DCC and/or UNC5A and/or B and/or C and/or D.

The percentage of netrin-1 overexpressing cases is given for each type of cancers for which expression of netrin-1 and its receptors have been quantified.

60% of metastatic breast cancer (Fitamant et al., PNAS 2008),

47% of non-small cell lung cancer (Delloye-Bourgeois et al., JNCI 2009),

38% of aggressive neuroblastoma (Delloye-Bourgeois et al., J. Exp. Med. 2009),
61% of pancreatic adenocarcinoma (Link et al., Annals of Chir. Onco. 2007; Dumartin et al., Gastro 2010),
100% of primary melanoma (n=7), melanoma metastasis (n=6) (Kaufmann et al., Cellular Oncology 2009),
76% of ovarian cancers (Panastasiou et al., Oncotarget 2011),
65% of glioblastoma,
>60% of acute myeloid leukemia and chronic lymphocytic leukemia
>50% of aggressive B-cell lymphoma,
30% of sarcoma,
40% of renal adenocarcinoma,
22% of head and neck cancers,
Testicular cancers (36% of embryonal carcinoma, 50% of teratoma, 100% of yolk sac tumors)
50% of kidney cancers,
26% of stomach cancers,
19% of uterus cancers.

REFERENCES

1. Serafini, T. et al. 1994. *Cell* 78:409-424.
2. Mazelin, L. et al. 2004. *Nature* 431:80-84.
3. Mehlen, P. et al. 2011. *Nat Rev Cancer* 11:188-197.
4. Mehlen, P. et al. 1998. *Nature* 395:801-804.
5. Llambi, F. et al. 2001. *Embo J* 20:2715-2722.
6. Tanikawa, C. et al. 2003. *Nat Cell Biol* 5:216-223.
7. Bredesen, D. E. et al. 2005. *Cell Death Differ* 12:1031-1043.
8. Mehlen, P., and A. Puisieux. 2006. *Nat Rev Cancer* 6:449-458.
9. Castets, M. et al. 2012. *Nature* 482(7386):534-7
10. Bernet, A. et al. 2007. *Gastroenterology* 133:1840-1848.
11. Fearon, E. R., et al. 1990. *Science* 247:49-56.
12. Thiebault, K. et al. 2003. *Proc Natl Acad Sci USA* 100:4173-4178.
13. Shin, S. K., et al. 2007. *Gastroenterology* 133:1849-1857.
14. Fitamant, J., et al. 2008. *Proc Natl Acad Sci USA* 105:4850-4855.
15. Delloye-Bourgeois, C. et al. 2009. *J Exp Med* 206:833-847.
16. Delloye-Bourgeois, C. et al. 2009. *J Natl Cancer Inst* 101:237-247.
17. Paradisi, A., C. et al. 2009. *Proc Natl Acad Sci USA* 106:17146-17151.
18. Dumartin, L., et al. 2010. *Gastroenterology* 138:1595-1606, 1606 e1591-1598.
19. Papanastasiou, A. D. et al. 2011. *Oncotarget* 2:363-367.
20. Mille, F. et al. 2009. *Cell Death Differ* 16:1344-1351.
21. Paradisi, A. et al. 2008. *Gastroenterology* 135:1248-1257.

The invention claimed is:

1. A method for treating cancer cells expressing or over-expressing netrin-1 and expressing a netrin-1 receptor, comprising administering an effective amount of a chemotherapeutic drug and of a netrin-1 interfering drug or a vector capable of expressing a netrin-1 interfering drug in vivo to a patient having cancer cells expressing or over-expressing netrin-1 and expressing a netrin-1 receptor, wherein the chemotherapeutic drug is able to induce an expression or over-expression of netrin-1 in the treated cancer cells, and the netrin-1 interfering drug is an antibody specifically binding to netrin-1 which upon binding to netrin-1 specifically inhibits the binding of netrin-1 to its receptor on the treated cancer cells and promotes netrin-1 receptors-induced apoptosis of the treated cancer cells expressing a netrin-1 receptor.

2. The method according to claim 1, wherein the netrin-1 interfering drug promotes netrin-1 receptors-induced apoptosis.

3. The method according to claim 1, wherein the chemotherapeutic drug is selected from the group consisting of doxorubicin, 5-fluorouracil (5FU), paclitaxel and cisplatin.

4. The method according to claim 1, wherein the chemotherapeutic drug and the netrin-1 interfering drug or a vector capable of expressing a netrin-1 interfering drug in vivo, are administered simultaneously, separately, or sequentially to said patient.

* * * * *

```
SEQUENCE LISTING

<160> NUMBER OF SEQ ID NOS: 14

<210> SEQ ID NO 1
<211> LENGTH: 446
<212> TYPE: PRT
<213> ORGANISM: Artificial Sequence
<220> FEATURE:
<223> OTHER INFORMATION: UNC5A-fusion protein UNC5A-TRAP

<400> SEQUENCE: 1

Met Asp Phe Gly Leu Arg Leu Ile Phe Leu Val Leu Val Leu Lys Gly
1               5                   10                  15

Val Leu Cys Leu Pro His Phe Leu Val Glu Pro Glu Asp Val Tyr Ile
                20                  25                  30

Val Lys Asn Lys Pro Val Leu Leu Val Cys Lys Ala Val Pro Ala Thr
            35                  40                  45

Gln Ile Phe Phe Lys Cys Asn Gly Glu Trp Val Arg Gln Val Asp His
        50                  55                  60

Val Ile Glu Arg Ser Thr Asp Gly Ser Ser Gly Leu Pro Thr Met Glu
65                  70                  75                  80

Val Arg Ile Asn Val Ser Arg Gln Val Glu Lys Val Phe Gly Leu
                85                  90                  95

Glu Glu Tyr Trp Cys Gln Cys Val Ala Trp Ser Ser Ser Gly Thr Thr
                100                 105                 110

Lys Ser Gln Lys Ala Tyr Ile Arg Ile Ala Tyr Leu Arg Lys Asn Phe
            115                 120                 125

Glu Gln Glu Pro Leu Ala Lys Glu Val Ser Leu Glu Gln Gly Ile Val
        130                 135                 140

Leu Pro Cys Arg Pro Pro Glu Gly Ile Pro Pro Ala Glu Val Glu Trp
145                 150                 155                 160

Leu Arg Asn Glu Asp Leu Val Asp Pro Ser Leu Asp Pro Asn Val Tyr
                165                 170                 175
```

```
Ile Thr Arg Glu His Ser Leu Val Val Arg Gln Ala Arg Leu Ala Asp
            180                 185                 190

Thr Ala Asn Tyr Thr Cys Val Ala Lys Asn Ile Val Ala Arg Arg Arg
            195                 200                 205

Ser Ala Ser Ala Ala Val Ile Val Tyr Gly Thr Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 2
<211> LENGTH: 444
<212> TYPE: PRT
<213> ORGANISM: Artificial Sequence
<220> FEATURE:
<223> OTHER INFORMATION: UNC5B-fusion protein UNC5B-TRAP

<400> SEQUENCE: 2

Met Asp Phe Gly Leu Arg Leu Ile Phe Leu Val Leu Val Leu Lys Gly
1               5                   10                  15

Val Leu Cys Tyr Phe Leu Gln Glu Pro Gln Asp Ala Tyr Ile Val Lys
            20                  25                  30

Asn Lys Pro Val Glu Leu Arg Cys Arg Ala Phe Pro Ala Thr Gln Ile
            35                  40                  45

Tyr Phe Lys Cys Asn Gly Glu Trp Val Ser Gln Asn Asp His Val Thr
        50                  55                  60

Gln Glu Gly Leu Asp Glu Ala Thr Gly Leu Arg Val Arg Glu Val Gln
65                  70                  75                  80

Ile Glu Val Ser Arg Gln Gln Val Glu Glu Leu Phe Gly Leu Glu Asp
                85                  90                  95
```

Tyr Trp Cys Gln Cys Val Ala Trp Ser Ser Ala Gly Thr Thr Lys Ser
            100                 105                 110

Arg Arg Ala Tyr Val Arg Ile Ala Tyr Leu Arg Lys Asn Phe Asp Gln
            115                 120                 125

Glu Pro Leu Gly Lys Glu Val Pro Leu Asp His Glu Val Leu Leu Gln
        130                 135                 140

Cys Arg Pro Pro Glu Gly Val Pro Val Ala Glu Val Glu Trp Leu Lys
145                 150                 155                 160

Asn Glu Asp Val Ile Asp Pro Thr Gln Asp Thr Asn Phe Leu Leu Thr
                165                 170                 175

Ile Asp His Asn Leu Ile Ile Arg Gln Ala Arg Leu Ser Asp Thr Ala
            180                 185                 190

Asn Tyr Thr Cys Val Ala Lys Asn Ile Val Ala Lys Arg Arg Ser Thr
            195                 200                 205

Thr Ala Thr Val Ile Val Tyr Gly Thr Asp Lys Thr His Thr Cys Pro
        210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 3
<211> LENGTH: 446
<212> TYPE: PRT
<213> ORGANISM: Artificial Sequence
<220> FEATURE:
<223> OTHER INFORMATION: UNC5C-fusion protein UNC5C-TRAP

<400> SEQUENCE: 3

Met Asp Phe Gly Leu Arg Leu Ile Phe Leu Val Leu Val Leu Lys Gly
1               5                   10                  15

```
Val Leu Cys Leu Pro His Phe Leu Ile Glu Pro Glu Ala Tyr Ile
         20                  25                  30

Val Lys Asn Lys Pro Val Asn Leu Tyr Cys Lys Ala Ser Pro Ala Thr
             35                  40                  45

Gln Ile Tyr Phe Lys Cys Asn Ser Glu Trp Val His Gln Lys Asp His
 50                      55                  60

Ile Val Asp Glu Arg Val Asp Glu Thr Ser Gly Leu Ile Val Arg Glu
 65                  70                  75                  80

Val Ser Ile Glu Ile Ser Arg Gln Gln Val Glu Glu Leu Phe Gly Pro
                 85                  90                  95

Glu Asp Tyr Trp Cys Gln Cys Val Ala Trp Ser Ser Ala Gly Thr Thr
                100                 105                 110

Lys Ser Arg Lys Ala Tyr Val Arg Ile Ala Tyr Leu Arg Lys Thr Phe
            115                 120                 125

Glu Gln Glu Pro Leu Gly Lys Glu Val Ser Leu Glu Gln Glu Val Leu
130                 135                 140

Leu Gln Cys Arg Pro Pro Glu Gly Ile Pro Val Ala Glu Val Glu Trp
145                 150                 155                 160

Leu Lys Asn Glu Asp Ile Ile Asp Pro Val Glu Asp Arg Asn Phe Tyr
                165                 170                 175

Ile Thr Ile Asp His Asn Leu Ile Ile Lys Gln Ala Arg Leu Ser Asp
            180                 185                 190

Thr Ala Asn Tyr Thr Cys Val Ala Lys Asn Ile Val Ala Lys Arg Lys
            195                 200                 205

Ser Thr Thr Ala Thr Val Ile Val Tyr Gly Thr Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
            435                 440                 445
```

<210> SEQ ID NO 4
<211> LENGTH: 446
<212> TYPE: PRT
<213> ORGANISM: Artificial Sequence
<220> FEATURE:
<223> OTHER INFORMATION: UNC5D-fusion protein UNC5D-TRAP

<400> SEQUENCE: 4

```
Met Asp Phe Gly Leu Arg Leu Ile Phe Leu Val Leu Val Leu Lys Gly
1               5                   10                  15

Val Leu Cys Leu Pro His Phe Ile Glu Glu Pro Asp Asp Ala Tyr Ile
            20                  25                  30

Ile Lys Ser Asn Pro Ile Ala Leu Arg Cys Lys Ala Arg Pro Ala Met
            35                  40                  45

Gln Ile Phe Phe Lys Cys Asn Gly Glu Trp Val His Gln Asn Glu His
        50                  55                  60

Val Ser Glu Glu Thr Leu Asp Glu Ser Ser Gly Leu Lys Val Arg Glu
65                  70                  75                  80

Val Phe Ile Asn Val Thr Arg Gln Gln Val Glu Asp Phe His Gly Pro
                85                  90                  95

Glu Asp Tyr Trp Cys Gln Cys Val Ala Trp Ser His Leu Gly Thr Ser
            100                 105                 110

Lys Ser Arg Lys Ala Ser Val Arg Ile Ala Tyr Leu Arg Lys Asn Phe
        115                 120                 125

Glu Gln Asp Pro Gln Gly Arg Glu Val Pro Ile Glu Gly Met Ile Val
    130                 135                 140

Leu His Cys Arg Pro Pro Glu Gly Val Pro Ala Ala Glu Val Glu Trp
145                 150                 155                 160

Leu Lys Asn Glu Glu Pro Ile Asp Ser Glu Gln Asp Glu Asn Ile Asp
                165                 170                 175

Thr Arg Ala Asp His Asn Leu Ile Ile Arg Gln Ala Arg Leu Ser Asp
            180                 185                 190

Ser Gly Asn Tyr Thr Cys Met Ala Ala Asn Ile Val Ala Lys Arg Arg
        195                 200                 205

Ser Leu Ser Ala Thr Val Val Val Tyr Gly Thr Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

| | | | | | | | | | | | |
|---|---|---|---|---|---|---|---|---|---|---|---|
|Ser|Arg|Glu|Glu|Met|Thr|Lys|Asn|Gln|Val|Ser|Leu|Thr|Cys|Leu|Val|
| | |355| | | |360| | | |365| |

Lys Gly Phe Tyr Pro Ser Asp Ile Ala Val Glu Trp Glu Ser Asn Gly
    370                        375                        380

Gln Pro Glu Asn Asn Tyr Lys Thr Thr Pro Val Leu Asp Ser Asp
385                         390                         395                      400

Gly Ser Phe Phe Leu Tyr Ser Lys Leu Thr Val Asp Lys Ser Arg Trp
                      405                       410                      415

Gln Gln Gly Asn Val Phe Ser Cys Ser Val Met His Glu Ala Leu His
            420                       425                      430

Asn His Tyr Thr Gln Lys Ser Leu Ser Leu Ser Pro Gly Lys
    435                       440                      445

<210> SEQ ID NO 5
<211> LENGTH: 672
<212> TYPE: DNA
<213> ORGANISM: Artificial Sequence
<220> FEATURE:
<223> OTHER INFORMATION: UNC5A DNA sequence

<400> SEQUENCE: 5

```
aagcttgccg ccaccatgga cttcggcctg cggctgatct tcctggtgct ggtgctgaag      60
ggcgtgctgt gcctgcccca cttcctggtg aacccgagg acgtgtacat cgtgaagaac     120
aagcccgtgc tgctggtgtg caaggccgtg cccgccaccc agattttctt caagtgcaac     180
ggcgagtggg tgcgccaggt ggaccacgtg atcgagagaa gcaccgacgg cagcagcggc     240
ctgcccacaa tggaagtgcg gatcaacgtg tcccggcagc aggtggaaaa ggtgttcggc     300
ctggaagagt actggtgcca gtgcgtggcc tggtccagca gcggcaccac caagagccag     360
aaggcctaca tccggatcgc ctacctgcgg aagaacttcg agcaggaacc cctggccaaa     420
gaggtgtccc tggaacaggg catcgtgctg ccctgcagac cccctgaggg cattccccct     480
gccgaggtgg aatggctgcg gaacgaggac ctggtggacc ccagcctgga ccccaatgtg     540
tacatcaccc gcgagcacag cctggtggtg agacaggccc gcctggccga caccgccaac     600
tacacctgtg tggccaagaa catcgtggcc agacggcgct gcctctgc cgccgtgatc     660
gtgtacggta cc                                                         672
```

<210> SEQ ID NO 6
<211> LENGTH: 666
<212> TYPE: DNA
<213> ORGANISM: Artificial Sequence
<220> FEATURE:
<223> OTHER INFORMATION: UNC5B DNA sequence

<400> SEQUENCE: 6

```
aagcttgccg ccaccatgga cttcggcctg cggctgatct tcctggtgct ggtgctgaag      60
ggcgtgctgt gctactttct gcaagaaccc caggacgcct acatcgtgaa gaacaagccc     120
gtggaactgc ggtgccgggc cttccctgcc acccaaatct acttcaagtg caacggcgag     180
tgggtgtccc agaacgacca cgtgacccag gaaggcctgg acgaggccac aggcctgaga     240
gtgcgcgagg tgcagatcga ggtgtcccgg cagcaggtgg aagaactgtt cggcctggaa     300
gattactggt gccagtgcgt ggcctggtct agcgccggca ccaccaagag cagacgggcc     360
tacgtgcgga tcgcctacct gcggaagaac ttcgaccagg aacccctggg caaagaggtg     420
cccctggacc acgaggtgct gctgcagtgc agacctcctg agggcgtgcc cgtggccgag     480
gtggaatggc tgaagaacga ggacgtgatc gaccctaccc aggataccaa cttcctgctg     540
```

```
accatcgacc acaacctgat catccggcag gcccggctga gcgacaccgc caattacacc    600
tgtgtggcca agaacatcgt ggccaagcgg cggagcacca ccgccaccgt gatcgtgtac    660
ggtacc                                                               666
```

<210> SEQ ID NO 7
<211> LENGTH: 672
<212> TYPE: DNA
<213> ORGANISM: Artificial Sequence
<220> FEATURE:
<223> OTHER INFORMATION: UNC5C DNA sequence

<400> SEQUENCE: 7

```
aagcttgccg ccaccatgga cttcggcctg cggctgatct tcctggtgct ggtgctgaag     60
ggcgtgctgt gcctgcccca cttcctgatc gagcccgaag aggcctacat cgtgaagaac    120
aagcccgtga acctgtactg caaggccagc cccgccaccc aaatctactt caagtgcaac    180
agcgagtggg tgcaccagaa agaccacatc gtggacgagc gggtggacga acaagcggc    240 ctgatcgtgc gcgaggtgtc catcgagatc agccggcagc aggtggaaga actgttcggc    300
cccgaggact actggtgcca gtgcgtggcc tggtctagcg ccggcaccac caagagccgg    360
aaggcctacg tgcggatcgc ctacctgaga aagaccttcg agcaggaacc cctgggcaaa    420
gaggtgtccc tggaacaaga agtgctgctg cagtgcagac ccccgaggg aatccccgtg    480 gccgaggtgg aatggctgaa gaacgaggac atcatcgacc ccgtggaaga tcggaacttc    540
tacatcacca tcgaccacaa cctgatcatc aagcaggccc ggctgagcga caccgccaac    600
tacacctgtg tggccaagaa catcgtggcc aagcggaagt ccaccaccgc caccgtgatc    660
gtgtacggta cc                                                        672
```

<210> SEQ ID NO 8
<211> LENGTH: 672
<212> TYPE: DNA
<213> ORGANISM: Artificial Sequence
<220> FEATURE:
<223> OTHER INFORMATION: UNC5D DNA sequence

<400> SEQUENCE: 8

```
aagcttgccg ccaccatgga cttcggcctg cggctgatct tcctggtgct ggtgctgaag     60
ggcgtgctgt gcctgcccca cttcatcgaa gagcccgacg acgcctacat catcaagagc    120
aaccccatcg ccctgcgctg caaggcccgc cccgccatgc agattttctt caagtgcaac    180
ggcgagtggg tgcaccagaa cgagcacgtg agcgaggaga ccctggacga gagcagcggc    240
ctgaaggtgc gggaagtgtt catcaacgtg acacggcagc aggtggaaga cttccacggc    300
cccgaagact actggtgcca gtgcgtggcc tggtcccacc tgggcaccag caagagccgg    360
aaggccagcg tgcggatcgc ctacctgcgg aagaacttcg agcaggaccc ccagggccgg    420
gaggtgccca tcgagggcat gatcgtgctg cactgcagac ccctgagggg cgtgcccgcc    480
gccgaggtgg aatggctgaa gaacgaggag cccattgaca gcgagcagga cgagaatatt    540
gacacccgcg ccgaccacaa tctgattatt agacaggccc ggctgagcga cagcggcaac    600
tacacctgta tggccgccaa catcgtggcc aagcggcgct ctctgtctgc caccgtggtg    660
gtgtacggta cc                                                        672
```

<210> SEQ ID NO 9
<211> LENGTH: 699
<212> TYPE: DNA

<213> ORGANISM: Artificial Sequence
<220> FEATURE:
<223> OTHER INFORMATION: Human IgG1 Fc coding sequence

<400> SEQUENCE: 9

```
ggtaccgaca agacccacac ctgtccccca tgccctgccc ctgaactgct gggaggcccc    60
agcgtgttcc tgttcccccc aaagcccaag acaccctga tgatcagccg gaccccgaa    120
gtgacctgcg tggtggtgga cgtgtcccac gaggaccctg aagtgaagtt caattggtac   180
gtggacggcg tggaagtgca acgccaag accaagccca gagaggaaca gtacaacagc    240
acctaccggg tggtgtccgt gctgaccgtg ctgcaccagg actggctgaa cggcaaagag   300
tacaagtgca aagtctccaa caaggccctg cctgccccca tcgagaaaac catcagcaag   360
gccaagggac agccccgcga gcctcaggtg tacacactgc cccccagccg ggaagagatg   420
accaagaacc aggtgtccct gacctgcctg gtcaagggct tttaccccag cgatatcgcc   480
gtggaatggg agagcaacgg ccagcccgag aacaattaca agaccacccc ccctgtgctg   540
gacagcgacg gctcattctt cctgtacagc aagctgaccg tggacaagag ccggtggcag   600
cagggcaacg tgttcagctg cagcgtgatg cacgaggccc tgcacaacca ctacacccag   660
aagtccctga gcctgagccc cggcaagtaa taatctaga                          699
```

<210> SEQ ID NO 10
<211> LENGTH: 21
<212> TYPE: RNA
<213> ORGANISM: Artificial Sequence
<220> FEATURE:
<223> OTHER INFORMATION: siRNA targeting netrin-1

<400> SEQUENCE: 10

```
aagcuggacg cagcaugaug c                                              21
```

<210> SEQ ID NO 11
<211> LENGTH: 25
<212> TYPE: DNA
<213> ORGANISM: Artificial Sequence
<220> FEATURE:
<223> OTHER INFORMATION: Forward primer

<400> SEQUENCE: 11

```
aaaagtactg caagaaggac tatgc                                          25
```

<210> SEQ ID NO 12
<211> LENGTH: 21
<212> TYPE: DNA
<213> ORGANISM: Artificial Sequence
<220> FEATURE:
<223> OTHER INFORMATION: Reverse primer

<400> SEQUENCE: 12

```
ccctgcttat acacggagat g                                              21
```

<210> SEQ ID NO 13
<211> LENGTH: 580
<212> TYPE: PRT
<213> ORGANISM: Homo sapiens

<400> SEQUENCE: 13

```
Gly Pro Gly Leu Ser Met Phe Ala Gly Gln Ala Ala Gln Pro Asp Pro
1               5                   10                  15

Cys Ser Asp Glu Asn Gly His Pro Arg Arg Cys Ile Pro Asp Phe Val
            20                  25                  30
```

```
            Asn Ala Ala Phe Gly Lys Asp Val Arg Val Ser Ser Thr Cys Gly Arg
                    35                  40                  45

Pro Pro Ala Arg Tyr Cys Val Val Ser Glu Arg Gly Glu Glu Arg Leu
                50                  55                  60

Arg Ser Cys His Leu Cys Asn Ala Ser Asp Pro Lys Lys Ala His Pro
            65                  70                  75                  80

Pro Ala Phe Leu Thr Asp Leu Asn Asn Pro His Asn Leu Thr Cys Trp
                            85                  90                  95

Gln Ser Glu Asn Tyr Leu Gln Phe Pro His Asn Val Thr Leu Thr Leu
                        100                 105                 110

Ser Leu Gly Lys Lys Phe Glu Val Thr Tyr Val Ser Leu Gln Phe Cys
                        115                 120                 125

Ser Pro Arg Pro Glu Ser Met Ala Ile Tyr Lys Ser Met Asp Tyr Gly
                        130                 135                 140

Arg Thr Trp Val Pro Phe Gln Phe Tyr Ser Thr Gln Cys Arg Lys Met
            145                 150                 155                 160

Tyr Asn Arg Pro His Arg Ala Pro Ile Thr Lys Gln Asn Glu Gln Glu
                            165                 170                 175

Ala Val Cys Thr Asp Ser His Thr Asp Met Arg Pro Leu Ser Gly Gly
                        180                 185                 190

Leu Ile Ala Phe Ser Thr Leu Asp Gly Arg Pro Ser Ala His Asp Phe
                        195                 200                 205

Asp Asn Ser Pro Val Leu Gln Asp Trp Val Thr Ala Thr Asp Ile Arg
                        210                 215                 220

Val Ala Phe Ser Arg Leu His Thr Phe Gly Asp Glu Asn Glu Asp Asp
            225                 230                 235                 240

Ser Glu Leu Ala Arg Asp Ser Tyr Phe Tyr Ala Val Ser Asp Leu Gln
                            245                 250                 255

Val Gly Gly Arg Cys Lys Cys Asn Gly His Ala Ala Arg Cys Val Arg
                        260                 265                 270

Asp Arg Thr Asp Ser Leu Val Cys Asp Cys Arg His Asn Thr Ala Gly
                        275                 280                 285

Pro Glu Cys Asp Arg Cys Lys Pro Phe His Tyr Asp Arg Pro Trp Gln
                        290                 295                 300

Arg Ala Thr Ala Arg Glu Ala Asn Glu Cys Val Ala Cys Asn Cys Asn
            305                 310                 315                 320

Leu His Ala Arg Arg Cys Arg Phe Asn Met Glu Leu Tyr Lys Leu Ser
                            325                 330                 335

Gly Arg Lys Ser Gly Gly Val Cys Leu Asn Cys Arg His Asn Thr Ala
                        340                 345                 350

Gly Arg His Cys His Tyr Cys Lys Glu Gly Tyr Tyr Arg Asp Met Gly
                        355                 360                 365

Lys Pro Ile Thr His Arg Lys Ala Cys Lys Ala Cys Asp Cys His Pro
                        370                 375                 380

Val Gly Ala Ala Gly Lys Thr Cys Asn Gln Thr Thr Gly Gln Cys Pro
            385                 390                 395                 400

Cys Lys Asp Gly Val Thr Gly Ile Thr Cys Asn Arg Cys Ala Lys Gly
                            405                 410                 415

Tyr Gln Gln Ser Arg Ser Pro Ile Ala Pro Cys Ile Lys Ile Pro Val
                        420                 425                 430

Ala Pro Pro Thr Thr Ala Ala Ser Ser Val Glu Glu Pro Glu Asp Cys
                        435                 440                 445
```

```
Asp Ser Tyr Cys Lys Ala Ser Lys Gly Lys Leu Lys Ile Asn Met Lys
    450                 455                 460
Lys Tyr Cys Lys Lys Asp Tyr Ala Val Gln Ile His Ile Leu Lys Ala
465                 470                 475                 480
Asp Lys Ala Gly Asp Trp Trp Lys Phe Thr Val Asn Ile Ile Ser Val
                485                 490                 495
Tyr Lys Gln Gly Thr Ser Arg Ile Arg Arg Gly Asp Gln Ser Leu Trp
                500                 505                 510
Ile Arg Ser Arg Asp Ile Ala Cys Lys Cys Pro Lys Ile Lys Pro Leu
            515                 520                 525
Lys Lys Tyr Leu Leu Leu Gly Asn Ala Glu Asp Ser Pro Asp Gln Ser
        530                 535                 540
Gly Ile Val Ala Asp Lys Ser Ser Leu Val Ile Gln Trp Arg Asp Thr
545                 550                 555                 560
Trp Ala Arg Arg Leu Arg Lys Phe Gln Gln Arg Glu Lys Lys Gly Lys
                565                 570                 575
Cys Lys Lys Ala
            580

<210> SEQ ID NO 14
<211> LENGTH: 1815
<212> TYPE: DNA
<213> ORGANISM: Artificial Sequence
<220> FEATURE:
<223> OTHER INFORMATION: human netrin-1 cDNA sequence

<400> SEQUENCE: 14
atgatgcgcg cagtgtggga ggcgctggcg gcgctggcgg cggtggcgtg cctggtgggc    60
gcggtgcgcg gcgggcccgg gctcagcatg ttcgcgggcc aggcggcgca gcccgatccc   120
tgctcggacg agaacggcca cccgcgccgc tgcatcccgg actttgtcaa tgcggccttc   180
ggcaaggacg tgcgcgtgtc cagcacctgc ggccggcccc cggcgcgcta ctgcgtggtg   240
agcgagcgcg gcgaggagcg gctgcgctcg tgccacctct gcaacgcgtc cgaccccaag   300
aaggcgcacc cgcccgcctt cctcaccgac ctcaacaacc cgcacaacct gacgtgctgg   360
cagtccgaga actacctgca gttcccgcac aacgtcacgc tcacactgtc cctcggcaag   420
aagttcgaag tgacctacgt gagcctgcag ttctgctcgc gcggccccga gtccatggcc   480
atctacaagt ccatggacta cgggcgcacg tgggtgccct ccagttcta ctccacgcag   540 tgccgcaaga gtacaaccg ccgcaccgc gcgcccatca ccaagcagaa cgagcaggag   600
gccgtgtgca ccgactcgca caccgacatg cgcccgctct cgggcggcct catcgccttc   660
agcacgctgg acgggcggcc ctcggcgcac gacttcgaca actcgcccgt gctgcaggac   720
tgggtcacgg ccacagacat ccgcgtggcc ttcagccgcc tgcacacgtt cggcgacgag   780
aacgaggacg actcggagct ggcgcgcgac tcgtacttct acgcggtgtc cgacctgcag   840
gtgggcggcc ggtgcaagtg caacggccac gcggcccgct cgtgcgcga ccgcaccgac   900 agcctggtgt gcgactgcag gcacaacacg gccggcccgg agtgcgaccg ctgcaagccc   960
ttccactacg accggccctg gcagcgcgcc acagcccgcg aagccaacga gtgcgtggcc  1020
tgtaactgca acctgcatgc ccggcgctgc cgcttcaaca tggagctcta caagctttcg  1080
gggcgcaaga gcggaggtgt ctgcctcaac tgtcgccaca caccgccgg ccgccactgc  1140 cattactgca aggagggcta ctaccgcgac atgggcaagc ccatcaccca ccggaaggcc  1200
tgcaaagcct gtgattgcca ccctgtgggt gctgctggca aaacctgcaa ccaaaccacc  1260
```

```
                                                                   -continued
ggccagtgtc cctgcaagga cggcgtgacg ggtatcacct gcaaccgctg cgccaaaggc    1320
taccagcaga gccgctctcc catcgccccc tgcataaaga tccctgtagc gccgccgacg    1380
actgcagcca gcagcgtgga ggagcctgaa gactgcgatt cctactgcaa ggcctccaag    1440
gggaagctga agattaacat gaaaaagtac tgcaagaagg actatgccgt ccagatccac    1500
atcctgaagg cggacaaggc gggggactgg tggaagttca cggtgaacat catctccgtg    1560
tataagcagg gcacgagccg catccgccgc ggtgaccaga gcctgtggat ccgctcgcgg    1620
gacatcgcct gcaagtgtcc caaaatcaag cccctcaaga agtacctgct gctgggcaac    1680
gcggaggact ctccggacca gagcggcatc gtggccgata aaagcagcct ggtgatccag    1740
tggcgggaca cgtgggcgcg gcggctgcgc aagttccagc agcgtgagaa gaagggcaag    1800
tgcaagaagg cctag                                                    1815
```